(12) United States Patent
Satoh et al.

(10) Patent No.: US 6,388,068 B1
(45) Date of Patent: May 14, 2002

(54) METHOD FOR PRODUCING FOREIGN POLYPEPTIDE IN PLANT INTERCELLULAR FLUID

(75) Inventors: Shinobu Satoh, Ibaraki; Susumu Masuda, Chiba, both of (JP)

(73) Assignee: Noda Institute for Scientific Research, Noda (JP)

( * ) Notice: Subject to any disclaimer, the term of this patent is extended or adjusted under 35 U.S.C. 154(b) by 0 days.

(21) Appl. No.: 09/512,342

(22) Filed: Feb. 24, 2000

(30) Foreign Application Priority Data

Feb. 26, 1999 (JP) ............................................ 11-051904

(51) Int. Cl.⁷ ............................................... C07H 21/04
(52) U.S. Cl. .................... 536/24.1; 536/23.1; 536/23.6
(58) Field of Search ........................ 435/6, 320.1, 410, 435/419; 536/23.1, 23.4, 23.6, 24.1; 800/287

(56) References Cited

U.S. PATENT DOCUMENTS 5,959,176 A     9/1999   Torikai et al. ............... 800/287

OTHER PUBLICATIONS

Susumu Masuda et al, DNA Cloning of a Novel Lectin–Like Xylem Sap Protein and Its Root–Specific Expression in Cucumber, Plant Cell Physiol. 40(11): pp 1177–1181 (1999).*

Shinobu Satoh et al., "Proteins and Carbohydrates in Xylem Sap form Squash Root.", Plant Cell Physiology, vol. 33, No. 7, pp. 841–847, (1992).

* cited by examiner

Primary Examiner—Sean McGarry
(74) Attorney, Agent, or Firm—Foley & Lardner

(57) ABSTRACT

The invention relates to a method for producing a foreign polypeptide comprising secreting the foreign polypeptide into an intercellular fluid of a plant and recovering the polypeptide therefrom; and to a promoter DNA for use in the method which is capable of directing the expression of the foreign polypeptide that is to be secreted. The method is extremely useful industrially, since the method enables to produce a foreign polypeptide in a plant xylem sap with high efficiency.

2 Claims, 7 Drawing Sheets

METHOD FOR PRODUCING FOREIGN POLYPEPTIDE IN PLANT INTERCELLULAR FLUID

FIELD OF THE INVENTION

The present invention relates to a method for producing a foreign polypeptide of interest by secreting the foreign polypeptide into a plant cell or plant body using a plant genetic recombination technique, a promoter for use in the method, and the like.

DESCRIPTION OF RELATED ART

Recombinant DNA techniques have enabled, through the use of appropriate transformants, the production of a foreign peptide by an organism that cannot produce the peptide naturally. Production systems using plants as hosts are also included in such techniques. Up to now, however, the use of plants as hosts for the production of foreign polypeptides have few practical applications.

For the production of a foreign polypeptide in a plant by a genetic engineering technique, the following method is known: a chimeric gene, in which the structural gene for the foreign polypeptide that is to be expressed in the plant is ligated at a site downstream of a promoter, is introduced in a plant cell to give a transformant plant cell; and the transformant plant cell is then regenerated by a conventional plant cell culture technique to generate a transgenic plant body capable of expressing the foreign polypeptide. A typical example of the promoter used in such a method is cauliflower mosaic virus 35S promoter (hereinafter, simply referred to as "35S promoter"). 35S promoter is known to direct the expression of a polypeptide of interest in a plant cell in a tissue-non-specific manner and, therefore, has been widely used as a promoter applicable to relatively general purposes particularly for laboratorial studies. However, in the tissue-non-specific expression, the expressed polypeptide is required to be isolated and purified from all kinds of tissues of the plant, which makes it difficult to produce the polypeptide at low cost, with good efficiency and in a large quantity. That is, in the case of production of a foreign polypeptide in various organs or tissues of a plant (such as fruit, tuber (root), leaf, or stem), polypeptides other than the polypeptide of interest are likely to contaminate as impurities in a large quantity. Therefore, such a production method involves higher cost for purification of the polypeptide compared to the conventional processes employing microbial fermentation.

Higher plants have adapted to their environments by developing into multi-cellular organisms and differentiating their tissues and even organs through a long process of evolution. The cells constituting the tissues and organs are individually surrounded by a cell wall, and the spaces between their cell walls are filled with an intercellular fluid (i.e., an apoplastic fluid). In particular, transport of water or other nutrient ingredients to various tissues becomes more important as plant bodies grow larger, and an intercellular fluid plays an important role in this transport. A vascular bundle found in a higher plant, particularly a pteridophyte, gymnosperm or angiosperm, which is composed of xylem (vessel and tracheids) and phloem (sieve tubes), is a representative organ having this transporting function. Xylem sap, which is one of the vascular bundle saps, contains water and inorganic nutrient ingredients absorbed from the soil, as well as other various substances synthesized in the root (e.g., plant hormones and carbohydrates). For example, it has been reported that when xylem sap from squash is subjected to SDS-polyacrylamide gel electrophoresis, several polypeptide bands are observed, demonstrating the presence of several kinds of polypeptides in the xylem sap in the relatively pure forms (S. Satoh et al., Plant Cell Physiol., 33, 841, 1992). If a foreign polypeptide can be secreted into a plant intercellular fluid in a tissue-specific manner, then a more economical processs for production of a foreign peptide compared to conventional tank fermentation methods with microbial or animal cultured cells will be realized. A recently developed related method is a method for the expression of a protein of interest in vascular bundles of the root using a promoter capable of directing the expression of the protein in a root-specific manner (Japanese Patent Application Laid-open No. 10-52273).

SUMMARY OF THE INVENTION

Under these situations, the present invention is directed to the production of a foreign polypeptide with high efficiency by secreting it into a plant intercellular fluid. That is, the object of the present invention is to provide a method for producing a foreign polypeptide in a plant without the need of a complicated purification, by utilizing the tissue-specific biofunction of the plant; and to provide a promoter, a signal peptide and the like for use in the method.

The present inventors have made extensive and intensive studies for overcoming the aforementioned problems. As a result, the inventors have found a method for producing a foreign polypeptide in a plant by utilizing the function to secret the polypeptide specifically into xylem sap (which is one of the plant intercellular fluids). The inventors have also found, as the intercellular fluid secretion function elements, a promoter and a signal sequence for the secretion of the polypeptide into xylem sap. Based on these findings, the inventors have succeeded in the establishment of a method for producing a foreign polypeptide in a plant intercellular fluid with high efficiency by constructing the xylem sap secretion promoter gene, a gene encoding a foreign polypeptide of interest and the plant secretion signal coding region, which led to the accomplishment of the invention.

According to the present invention, there is provided a method for producing a foreign polypeptide of interest in a plant, comprising secreting the foreign polypeptide into an intercellular fluid of the plant and then recovering the foreign polypeptide therefrom.

In this method, the intercellular fluid may be a vascular bundle sap. In this case, the vascular bundle sap may be a xylem sap.

In the method, the plant may be a plant cell or plant body. In this case, the plant cell or plant body may be of a monocotyledonous or dicotyledonous plant, or may be of a plant selected from the group consisting of poaceous, leguminous, solanaceous, brassicaceous, cucurbitaceous, umbelliferous and asteraceous plants.

In the method, the foreign polypeptide of interest may be human serum albumin.

The present invention also provides a promoter DNA capable of directing the expression of both a signal peptide for the secretion of a foreign polypeptide of interest into an intercellular fluid of a plant and the foreign polypeptide.

The promoter DNA may be:

(a) a promoter DNA comprising the nucleotide sequence depicted in SEQ ID NO: 1; or (b) a promoter DNA having addition, deletion or substitution of one or a plurality of nucleotides in the nucleotide sequence depicted in SEQ ID NO: 1 and capable of directing the expression of a foreign polypeptide that is secreted into an intercellular fluid of a plant.

The promoter DNA may be:

(a) a promoter DNA comprising the nucleotide sequence depicted in SEQ ID NO: 2; or (b) a promoter DNA having addition, deletion or substitution of one or a plurality of nucleotides in the nucleotide sequence depicted in SEQ ID NO: 2 and capable of directing the expression of a foreign polypeptide that is secreted into an intercellular fluid of a plant.

The present invention also provides a recombinant DNA comprising the above-described promoter DNA and a structural gene encoding the foreign polypeptide of interest.

The present invention also provides a recombinant DNA comprising the above-described promoter DNA, a structural gene encoding the foreign polypeptide of interest and a gene encoding a signal peptide.

The present invention also provides a signal peptide gene encoding:

(a) a peptide comprising the amino acid sequence depicted in SEQ ID NO: 3; or (b) a peptide having addition, deletion or substitution of one or a plurality of amino acid residues in the amino acid sequence depicted in SEQ ID NO: 3 and having a signal peptide activity.

The present invention also provides a recombinant DNA comprising the promoter DNA, a structural gene encoding a foreign polypeptide of interest and a terminator.

The present invention also provides a recombinant DNA comprising the above-described promoter DNA, a structural gene encoding a foreign polypeptide of interest, a gene encoding a signal peptide and a terminator.

The present invention also provides an expression vector containing the promoter DNA.

The present invention also provides an expression vector containing the recombinant DNA.

The present invention also provides a plant cell transformed with the expression vector.

The present invention also provides a plant body regenerated from the plant cell.

The present invention also provides a method for producing a foreign polypeptide of interest, comprising cultivating the plant body.

This specification includes part or all of the contents as disclosed in the specification and/or drawings of Japanese Patent Application No. 11-51904, which is a priority document of the present application and incorporated herein by reference in its entirety.

The above and other objects, effects, features and advantages of the present invention will become more apparent from the following description of embodiments thereof.

DETAILED DESCRIPTION OF THE INVENTION

Figure 1:
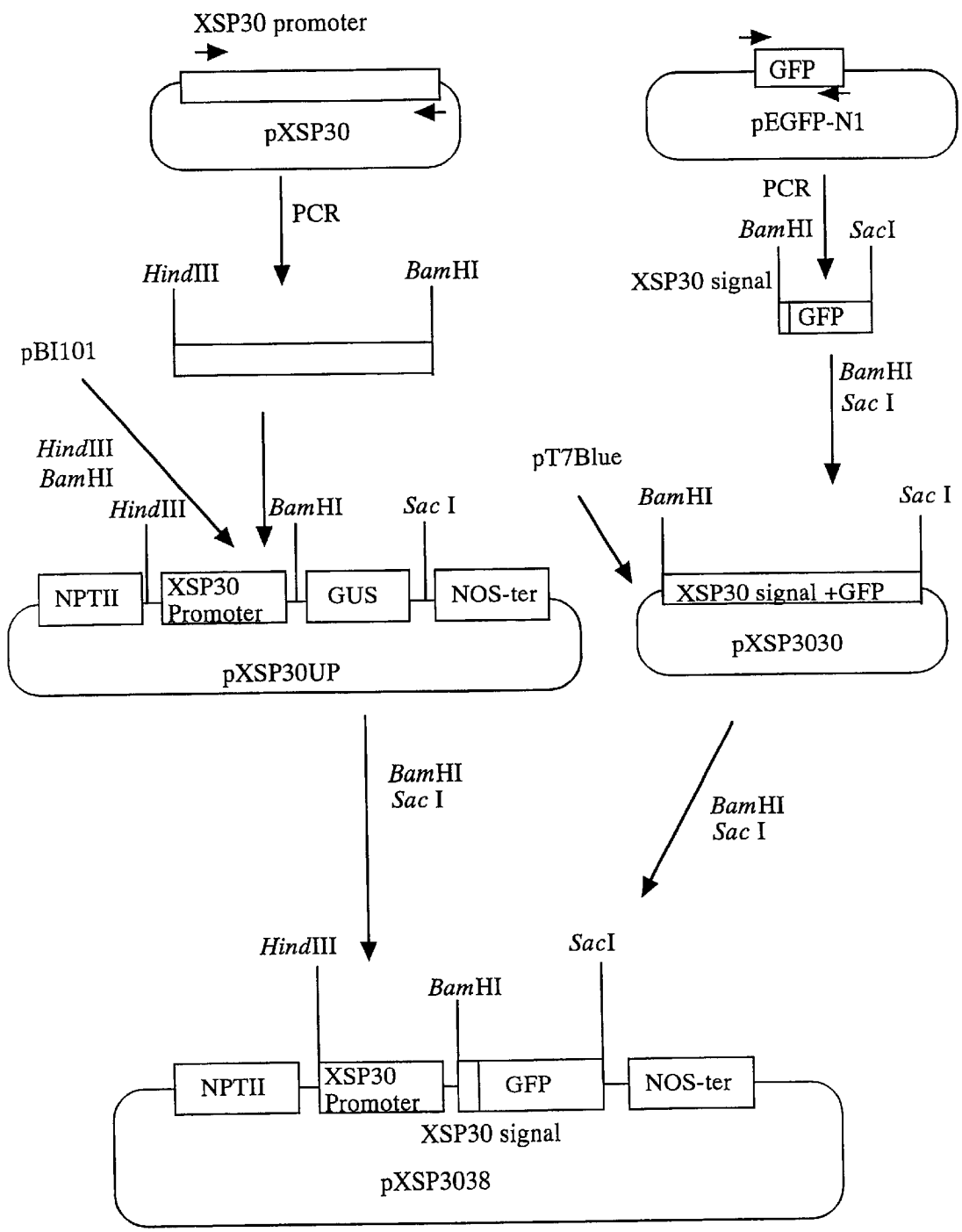
FIG. 1 illustrates the construction of an expression vector PXSP3038.

Hereinbelow, the present invention will be described in detail.

In the present invention, conventional genetic engineering techniques may be employed, such as those described in J., Sambrook, E., F., Friscll, and T., Maniatis, Molecular Cloning 2nd ed., 1989; and D., H., Clover, DNA Cloning, 1985, The plant intercellular fluid used in the present invention includes, for example, a vascular bundle sap (e.g., xylem sap, tracheid sap, phloem sap) from a plant, an exudate from a vitaceous or cornaceous tree, sugar maple tree, coconut palm tree or the like.

The plant from which the intercellular fluid is collected or the plant used as a host for secreting the foreign polypeptide of interest according to the present invention may be of any species, provided that it has an intercellular fluid, such as a pteridophyte, an angiosperm or a gymnosperm. More specifically, the plant may be a monocotyledonous or dicotyledonous plant, such as a poaceous, leguminous, solanaceous, brassicaceous, cucurbitaceous, umbelliferous or asteraceous plant. Specific examples of the plant include monocotyledonous plants, such as rice plant and plants of corn, barley and wheat; and dicotyledonous plants, such as plants of soy bean, field pea, tomato, potato, eggplant, cucumber, melon, carrot and celery.

The foreign polypeptide produced in a plant according to the present invention may be an industrially useful polypeptide that is derived from a plant other than a host plant, a microorganism or an animal but cannot be produced by the host plant. Specific examples of the foreign polypeptide include, but are not limited to, human serum albumin, green fluorescent protein (GFP), peptide hormones (e.g., insulin, human growth hormone), bioactive factor preparations (e.g., interferon), enzymes (e.g., urokinase, peroxidase), vaccines (e.g., influenza virus vaccines), fiber proteins (e.g., fibroin), and plant disease resistance proteins (e.g., chitinase, $\beta$-1,3-glucanase). The structural genes for these foreign polypeptides have known structures and are available relatively readily.

The promoter DNA and the gene encoding both capable of directing the expression of the secretion function of the foreign polypeptide in a plant intercellular fluid according to the present invention can be constructed as follows.

At first, the acetone-precipitation fraction of the plant intercellular fluid is analyzed by the SDS-PAGE method, and a gel band corresponding to the purified major polypeptide contained in the intercellular fluid is excised. The N-terminal amino acid sequence of the polypeptide is determined using, for example, Protein Sequencer 477A (ABI). On the other hand, cDNA is prepared using, as a template, mRNA isolated from the same plant body by a conventional method. PCR is performed using the cDNA as a template and synthetic mix primers designed based on the determined N-terminal amino acid sequence. The amplified product is cloned into a plasmid vector. Based on the DNA sequence, various types of primer DNAs are prepared. Using the primer DNAs, DNAs containing the fragments of the major polypeptide DNA are specifically amplified by an appropriate PCR method (e.g., RT-PCR method, 5'-RACE method or 3'-RACE method) and then ligated, thereby preparing a cDNA clone containing the full length DNA of the polypeptide.

Alternatively, a cDNA clone encoding a foreign polypeptide that is to be secreted into a plant intercellular fluid may also be prepared by screening the expression library of the cDNA derived from the root using anti-serums to all of the polypeptides contained in the xylem sap. By comparing the amino acid sequence deduced from the cDNA sequence thus prepared to the N-terminal amino acid sequence experimentally determined above, a signal sequence region can be specified.

A promoter region can be prepared as follows, for example. Genomic DNA is prepared from the leaf of the same plant, and partially digested with suitable enzymes. The resultant fragment is ligated to a phage-derived vector arm, which is then packaged in vitro to generate phage particles. *Escherichia coli* (hereinafter, simply referred to as "*E. coli*") is infected with the phage particles to form plaques on an agar medium. The transformants may be recovered from the plaques and used as a genomic library for screening a genomic clone that is assumed to contain the promoter region of the present invention.

Alternatively, a primer specific to the promoter region may be synthesized based on the sequence of a known cDNA region. The primer may be used in combination with a non-specific primer to perform PCR by a method for specifically amplifying a unknown genomic DNA region (i.e., TAIL-PCR method), thereby preparing a sequence containing the promoter region immediately adjacent to the cDNA. In this manner, a genomic clone that is assumed to contain a promoter region of the present invention can be isolated.

A DNA fragment assumed to contain the cDNA and the promoter region may be subcloned into a plasmid vector to which DNA of interest can be inserted readily and in which the inserted DNA can be analyzed readily. Examples of the plasmid include is of which DNA can be readily prepared or which can be assayed readily (e.g., pUC18, pUC19, PBLUESCRIPT KS+, pBLUESCRIPT KS−; Takara Shuzo Co., Ltd.), thereby preparing recombinant plasmid DNA. The DNA can be sequenced by a cycle sequencing method utilizing a combination of PCR methods such as those described by Sanger et al. (J. Mol. Biol., 94, 441, 1975; Proc. Natl. Acad. Sci., 74, 5463, 1977) and by Saiki et al. (Science, 230, 1350, 1985).

Specific examples of the promoter DNA of the present invention are those depicted in SEQ ID NO:1 (hereinafter, referred to as "promoter I") and SEQ ID NO:2 (hereinafter, referred to as "promoter II"). The promoter DNA of the present invention also includes variants of these promoter DNAs in which one or a plurality of amino acid residues are added, deleted or substituted in SEQ ID NO:1 and SEQ ID NO: 2, provided that they have the function to induce the expression of a foreign polypeptide of interest. In addition, the promoter DNA of the present invention also includes the nucleotide sequences of SEQ ID NO:1 and SEQ ID NO:2 having at the 3' terminus the addition of a nucleotide sequence that increases the translation efficiency or having the deletion of the 5' terminal region, provided that they have the above-mentioned function.

A typical example of the gene encoding a signal peptide of the present invention is a gene encoding a peptide comprising an amino acid sequence depicted in SEQ ID NO:3. The present invention also includes variants of this gene having addition, deletion or substitution of one or a plurality of amino acid residues in SEQ ID NO:3, provided that it can encode the peptide.

A recombinant DNA containing the promoter DNA of the present invention, a structural gene encoding a foreign polypeptide of interest and a signal peptide coding gene can be prepared by inserting the signal peptide coding gene between the promoter DNA and the structural gene.

Each of the above-described recombinant DNAs may be additionally integrated with a terminator at the downstream region to prepare a recombinant DNA with an increased foreign polypeptide expression efficacy. As used herein, the term "terminator" refers to an element capable of efficiently terminating the transcription of the structural gene of interest in a plant cell, which is usually located downstream of the structural gene of the polypeptide. The terminator used in the present invention is not particularly limited, and any type of terminator may be used, such as a plant gene-derived terminator for nopaline synthase gene and terminators for garlic virus GV1 and GV2 genes.

These types of recombinant DNAs can be prepared relatively readily by a conventional genetic engineering procedure. That is, the promoter DNA of the present invention, the structural gene for the foreign polypeptide, the gene encoding the signal peptide and the terminator may be separately digested with restriction enzymes (e.g., BamHI, SacI, XhoI, XbaI, EcoRV, EcoRI, SmaI, HindIII) so that their functions can be retained, and the resultant fragments may be ligated together in an appropriate manner, thereby giving a desired type of recombinant DNA.

The expression vector of the present invention contains the recombinant DNA prepared as described above and a vector which is autonomously replicable in a host chromosome-independent manner and is capable of inheriting stably. The expression vector can be prepared relatively readily by a conventional genetic engineering procedure. Examples of the vector include pBI 101 (CLONTECH), pBI N19 (Nuc. Acid. Res., 12, 8711–8721, 1984), Agrobacterium Ti plasmid and Ri plasmid. A plant virus, such as cauliflower mosaic virus, may also be utilized as the vector.

The transformant plant cell of the present invention can be prepared with the expression vector. The transformation method applicable in the present invention is a known method, such as an electrical gene transfer method (electrical gene transfer into a protoplast: electroporation), a direct gene transfer method using a particle gun, and a method of infecting a plant tissue with Agrobacterium cell. In the present invention, however, what type of method is employed is not critical, provided that the expression vector can be introduced into a plant and integrated into the plant chromosome genetically stably.

An exemplified method in which Agrobacterium Ti plasmid is used as the vector is illustrated in the following.

A gene of interest can be introduced into a plant body utilizing such a nature of a bacterium belonging to Agrobacterium that, when a plant is infected with the bacteria, a part of plasmid DNA in the bacteria is transferred into the genome of the plant. For example, upon the infection of a plant, *Agrobacterium tumefaciens* induces so-called crown-gall tumors in the plant. This is caused by the transfer of a region called "T-DNA (Transferred DNA)" located on Ti plasmid in the bacteria into the plant upon the infection, whereby the region is integrated into the genome of the plant. For the transfer of the T-DNA region into the plant and its integration into the genome of the plant, Ti plasmid requires Vir region. Based on this mechanism, the transformant plant cell of the present invention can be prepared by infecting a seed, a leaf disc or a protoplast of a host plant with *Agrobacterium tumefaciens* cells carrying Ti plasmid having T-DNA region, the recombinant DNA of the present invention inserted in the T-DNA region and Vir region therein.

The transgenic plant of the present invention can be prepared from the transformant plant cell by a conventional plant cell culture method as described in, for example, Hirohumu Uchiyama, "Plant Gene Manipulation Manual—Method for Generation of Transgenic Plant", Kodansha press, pp.27–55, 1990; S. B. Gelvin, R. A. Schilperoot and D. P. S. Versam, "Plant Molecular Biology/Manual", Kluwer Academic Publishers press, 1988; or Valvekens et al., Proc. Natl. Acad. Sci., 85:5536–5540, 1988.

An exemplified method for introducing an expression vector of interest into a plant by the use of Agrobacterium cells and regenerating the transformed plant cell into a plant body uutilizing cucumber as the plant is illustrated in the following.

Cucumber seeds are sown onto MS plate and cultivated sterilely in a conventional manner. A cut piece of cotyledon or hypocotyl is subjected to callus culture on a regeneration plate. Agrobacterium cells that has been transfected with Ti plasmid having the recombinant DNA of the present invention and kanamycin- and hygromycin-resistance genes inserted therein (i.e., the expression vector of the present invention) are cultured, diluted and then dispensed into tubes. A cut piece of cotyledon or hypocotyl is soaked in the tube and then co-cultured with the Agrobacterium cells on a regeneration plate for several days. When the Agrobacterium cells are grown enough to be observed by the naked eye, the bacterial cells are removed from the medium and the piece was further cultured on the regeneration plate for additional several days. The piece is finally cultured on a regeneration plate. The cultured piece is transferred to a newly prepared plate successively. During the culture, transformed piece continues to grow to calluses. A non-transformed piece color-changes into brown due to the selection with antibiotics. The culture is continued until the transformant grows to have the size of about 5 mm and form a callus. When a fully grown callus appears, it is excised with a knife so as to remove the cotyledon or hypocotyl therefrom, and then transferred onto a selection plate. After rooting, the callus is set on a rock wool immersed on an inorganic saline medium. Thus, the transgenic plant body of the present invention can be generated.

The rooted plant may be transplanted in soil immersed in an inorganic saline medium to generate its seeds. The seeds may be subjected to sterile treatment and then sown onto MS medium, thereby generating germinated transgenic plant bodies. The transgenic plant bodies can be confirmed for the success in transformation by extracting DNA therefrom in a conventional manner, digesting the DNA with suitable restriction enzymes, and then subjecting the digested DNA fragments to Southern hybridization using the promoter DNA of the present invention as a probe.

Hereinbelow, the present invention will be illustrated in more detail with reference to the following examples. It should be understood, however, that the invention is not limited to the examples.

EXAMPLES

The media used in the examples have the following compositions.
(i) Media for Cucumber
(a) MS Medium
A medium prepared by dissolving MUPASHIGE AND SKOOG (Flow Laboratories) (4.4 g) in distilled water (1 L), adjusting to pH 5.8 with 1 M KOH, further adding Gelrite (Wako Pure Chemical Industries. Ltd.) (2.5 g) thereto, and then sterilizing the mixed solution in an autoclave.

(b) MS-BA Medium
A medium containing sucrose (30 g), 6-benzylaminopurine (BA) (2.0 μg/mL) and abscisic, acid (ABA) (1.0 μg/mL) in MS medium.
(c) MS-BAC Medium
A medium containing Claforan (200 μg/mL) in MS-BA medium.
(d) MS-BACK Medium
A medium containing kanamycin (100 μg/mL) in MS-BAC medium.
(e) MS-CK Medium
A medium containing kanamycin (100 μg/mL) and Claforan (200 μg/mL) in MS medium.
(ii) Media for Bacteria
(a) L-Medium
A medium prepared by dissolving Bacto Tryptone (Difco) (10 g), Bacto Yeast Extract (Difco) (5 g) and NaCl (10 g) in distilled water (1 L), adjusting to pH 7.0 with 5N NaOH, and then sterilizing the mixed solution in an autoclave. If used in the form of a plate, the mixed solution is added with agar (15 g).
(b) NZY Medium
A medium prepared by dissolving yeast extract (5 g), NZ amine (10 g), NaCl (5 g) and $MgSO_4 \cdot 7H_2O$ (2 g) in distilled water (1 L), adjusting to pH 7.5 with 5N NaOH, and then sterilizing the mixed solution in an autoclave. If used in the form of a plate, the mixed solution is added with agar (Difco) (15 g).
(c) Top agar
A medium containing Agarose-II (Dojin) (0.7 g) in NZY medium (100 mL).

Example 1

Isolation of Promoter I

A gene encoding the major protein in xylem sap was isolated, and the promoter region on the gene was obtained. The screening methods are illustrated in the following.
(1) Collection of Cucumber Xylem Sap
The stem of 6-week-old cucumber (*Cucumis sativus* cv., Shimoshirazu-jibai) was cut 15–30 cm above the soil level so as to contain no leaf. The first several drops of the xylem sap (exudate) from the cut surface were discarded, and the cut surface of the stem was washed with sterile water. A tube was connected to the stem to collect the xylem sap in the tube on ice.
(2) Detection of the Protein in Xylem Sap
The collected xylem sap was concentrated with acetone. An aliquot (300 μL) of the xylem sap was analyzed by SDS-PAGE. As a result, a band corresponding to the major protein observed at the position of about 30 kDa on the gel, which was designated "XSP30 (xylem sap protein 30)". The XSP30-containing gel portion was excised from the acrylamide gel, and XSP30 was eluted in an elution buffer (0.1 M sodium acetate, 0.1% SDS, pH 8.5). The N-terminal amino acid sequence of XSP30 contained in the elution buffer was determined, demonstrating that it had the sequence as depicted in SEQ ID NO:4. To determine the entire primary structure of XSP30, cDNA encoding XSP30 was cloned by PCR method in the following manner.
(3) Preparation of mRNA and cDNA from Cucumber Root
A cucumber root was crushed in the presence of liquid nitrogen, and mRNA was isolated therefrom by the SDS-phenol method (Nosonbunka-sha publ., "Biotechnology Experimental Manual for Plant", 1989). cDNA was synthesized using the isolated mRNA as a template and RNA PCR kit (AMV) Ver. 2.1 (Takara Shuzo Co., Ltd.). In this reaction, Oligo dT adapter primer provided in the kit was used as a primer.

(4) Preparation and Cloning of XSP30 cDNA and Fragments Thereof

Based on the N-terminal amino acid sequence of XSP30 determined in the above step using a protein sequencer, mix primers [primer 1 (SEQ ID NO:5) and primer 2 (SEQ ID NO:6)] were designed and synthesized. PCR was performed using the cDNA prepared in the above step as a template and the primer mix [primer 1 (SEQ ID NO:5)] and the adapter primer provided in the kit at a program: 94° C. for 1 min.; 45° C. for 1 min.; and 72° C. for 2 min., for 30 cycles. The PCR-amplified product was diluted 100 times and used as a template for PCR. The PCR was performed using the mix primer [primer 2 (SEQ ID NO:6)] and the adapter primer provided in the kit at a program: 94° C. for 1 min.; 55° C. for 1 min.; and 72° C. for 2 min., for 30 cycles, thereby giving an amplified product of about 800 bp in length. In the amplification reaction, Ex Taq DNA polymerase (Takara Shuzo Co., Ltd.) and a buffer and dNTPs provided therein were used according to the manufacturer's instructions, and a thermal cycler "GENE AMP PCR SYSTEM 9600" (Perkin-Elmer) was also used. The product was ligated to plasmid vector pT7Blue (Novagen) using a ligation kit (Takara Shuzo Co., Ltd.) to give a recombinant plasmid. The reaction solution containing the recombinant plasmid was added with *E. coli* JM109 competent cells (Toyobo co., Ltd.) to cause the transformation of the cells with the recombinant plasmid, and then plated on LB plate containing ampicillin (100 μg/mL). The plate was incubated at 37° C. overnight, and plasmid DNA was prepared from the grown clones on the plate. The inserted DNA was sequenced on a DNA sequencer (Model 373S, Applied Biosystems) using Dye Terminator Cycle Sequencing FS Ready Reaction Kit (Applied Biosystems). The amino acid sequence deduced from the nucleotide sequence was found to correspond to the amino acids 16–23 of the above-determined N-terminal amino acid sequence of XSP30, clearly demonstrating that a fragment of the desired gene was successfully amplified.

| Primer 1: gtnccnggnaaytayggntaygg | (SEQ ID NO:5) |
|---|---|
| Primer 2: tayggngtnggntayggnggngtncc | (SEQ ID NO:6) |

A nucleotide sequence containing the region determined in the above step and the 3'-downstream region thereof was prepared by 3' RACE method in the following manner. In this method, a kit "Full RACE Core Set" (Takara Shuzo Co., Ltd.) was used. At first, a nucleotide sequence shown below (see "primer 3") was selected from the nucleotide sequence determined in the above step and then synthesized as an upstream primer for use in PCR, which was named "primer 3" (SEQ ID NO:7). A single-stranded cDNA was synthesized with a reverse transcriptase using mRNA isolated from a cucumber root as a template and Oligo dT-3sites Adapter Primer provided in the kit. PCR was performed using the resultant single-stranded cDNA as a template and primer 3 and 3sites Adapter Primer provided in the kit, thereby giving an amplified product of about 700 bp in length. The product was ligated to plasmid vector pT7Blue (Novagen) using a ligation kit (Takara Shuzo Co., Ltd.) to give a recombinant plasmid. The reaction solution containing the recombinant plasmid was added with *E. coli* JM109 competent cells (Toyobo Co., Ltd.) to cause the transformation of the cells with the recombinant plasmid, and then plated on LB plate containing ampicillin (100 μg/mL). The plate was incubated at 37° C. overnight, and plasmid DNA was prepared from the grown clones on the plate. The inserted DNA was sequenced on a DNA sequencer (Model 373S, Applied Biosystems) using Dye Terminator Cycle Sequencing FS Ready Reaction Kit (Applied Biosystems). As a result, it was confirmed that the 3'-terminal region of XSP30 cDNA was successfully amplified.

| Primer 3: cagaagaatgacggaaccata | (SEQ ID NO:7) |
|---|---|

The nucleotide sequence of the 5' terminal region of XSP30 cDNA was determined by 5'-RACE method based on the sequence determined in the above step in the following manner. In this method, a kit "5'-Full RACE Core Set" (Takara Shuzo Co., Ltd.) was used.

Based on the sequence determined in the above step, primer 4 (SEQ ID NO:8), primer 5 (SEQ ID NO:9), primer 6 (SEQ ID NO:10), primer 7 (SEQ ID NO:11) and primer 8 (SEQ ID NO:12) shown below were synthesized. A single-stranded cDNA was synthesized with a reverse transcriptase using the mRNA isolated from cucumber root as a template and primer 4 (SEQ ID NO:8). The resultant single-stranded cDNA was used as a template for two-successive PCR. The first stage PCR was performed using the combination of primer 5 (SEQ ID NO:9) and primer 6 (SEQ ID NO:10), and subsequently the second stage PCR was performed using the combination of primer 7 (SEQ ID NO:11) and primer 8 (SEQ ID NO:12), thereby giving an amplified product of about 700 bp in length. The product was ligated to plasmid vector pT7Blue using a ligation kit to give a recombinant plasmid. The reaction solution containing the recombinant plasmid was added with *E. coli* JM109 competent cells to cause the transformation of the cells with the recombinant plasmid, and then plated on LB plate containing ampicillin (100 μg/mL). The plate was incubated at 37° C. overnight, and plasmid DNA was prepared from the grown clones on the plate. The inserted DNA was sequenced on a DNA sequencer using Dye Terminator Cycle Sequencing FS Ready Reaction Kit (Applied Biosystems). As a result, it was confirmed that a nucleotide sequence containing the 5'-terminal region of XSP30 cDNA was obtained.

From the results of the RT-PCR, the 3'-RACE and the 5'-RACE performed in the above steps, the nucleotide sequence of the full-length XSP30 cDNA (SEQ ID NO:13) was clearly determined. Since only one initiation methionine was found in the nucleotide sequence (SEQ ID NO:13), the full-length amino acid sequence of XSP30 (SEQ ID NO:14) could be deduced. In addition, since the N-terminal region of the mature XSP30 has the nucleotide sequence of SEQ ID NO:4, it was found that XSP30 had a signal sequence consisting of 21 amino acid residues (see SEQ ID NO:3).

| Primer 4: 5'-agaagtcaagcaatagttttt-3' | (SEQ ID NO:8) |
|---|---|
| Primer 5: 5'-aaaaacttcagcagccaa-3' | (SEQ ID NO:9) |
| Primer 6: 5'-ggggtcataaataaagca-3' | (SEQ ID NO:10) |
| Primer 7: 5'-agcaaaatttatcattca-3' | (SEQ ID NO:11) |
| Primer 8: 5'-gtagtaagtgagtgtggt-3' | (SEQ ID NO:12) |

For the preparation of a nucleotide sequence upstream of the XSP30 genome determined in the above steps, primers were designed based on the nucleotide sequence of the XSP30 cDNA. TAIL-PCR was performed using the primers according to the method described in "The Plant Journal", vol.8, pp.457–463, 1995 to clone the upstream promoter region of XSP30. The PCR was performed in the following manner.

At first, based on the nucleotide sequence of the XSP30 cDNA, primer 9 (SEQ ID NO:15), primer 10 (SEQ ID NO:16), primer 11 (SEQ ID NO:17) and primer 12 (SEQ ID NO:18) shown below were synthesized. PCR was performed using the combination of primer 12 (SEQ ID NO:18) and primer 9 (SEQ ID NO:15) and cucumber genomic DNA as a template at a program: 93° C. for 1 min.; and 95° C. for 1 min., for 1 cycle; at a program: 94° C. for 1 min.; 60° C. for 1 min.; and 72° C. for 2.5 min., for 5 cycles; at a program: 94° C. for 1 min.; 25° C. for 3 min,; and after gradually heating to 72° C. over 3 min., 72° C. for 2.5 min., for 1 cycle; at a program: 94° C. for 1 min.; 68° C. for 1 min.; 72° C. for 2.5 min.; 94° C. for 30 sec.; 68° C. for 1 min.; 72° C. for 2.5 min.; 94° C. for 30 sec.; 44° C. for 1 min.; and 72° C. for 2.5 min., for 15 cycles; and then at a program: 72° C. for 2.5 min., for 1 cycle. Using the PCR product as a template in the form of a diluted solution and the combination of primer 12 (SEQ ID NO:18) and primer 10 (SEQ ID NO:16), PCR was performed at a program: 94° C. for 30 sec,; 64° C. for 1 min.; 72° C. for 2.5 min.; 94° C. for 30 sec.; 64° C. for 1 min.; 72° C. for 2.5 min.; 94° C. for 30 sec.; 44° C. for 1 min.; and 72° C. for 2.5 min., for 12 cycles and then at a program: 72° C. for 2.5 min., for 1 cycle. Using the PCR product as a template in the form of a diluted solution and the combination of primer 12 (SEQ ID NO:18) and primer 11 (SEQ ID NO:17), PCR was performed at a program: 94° C. for 60 sec.; 44° C. for 1 min.; and 72° C. for 2.5 min., for 20 cycles and then at a program: 72° C. for 5 min., for 1 cycle, thereby giving an amplified fragment of about 2,000 bp in length. This product was cloned into pT7Blue, and the entire nucleotide sequence of the plasmid DNA was then sequenced on a fluorescent sequencer (ABI) using Taq Dye Deoxy Terminator Cycle Sequencing Kit (ABI) (see SEQ ID NO:1). As a result, it was confirmed that the clone contained an about 1,900 bp upstream region of XSP30 (i.e., a promoter of the present invention), which was designated "Promoter I".

| Primer 9: 5'-tcttctgggtccatttcttgttagg-3' | (SEQ ID NO:15) |
| Primer 10: 5'-ctttccgtgacttcccaactttgtg-3' | (SEQ ID NO:16) |
| Primer 11: 5'-cgtcacatggtgataatcgagttgg-3' | (SEQ ID NO:17) |
| Primer 12: 5'-ngtcgaswganawgaa-3' | (SEQ ID NO:18) |

Example 2

Isolation of Promoter II

Using mRNA isolated from a cucumber root, a cDNA library was constructed. The cDNA library was screened with anti-xylem sap serum prepared by immunizing a rat, and several positive clones were obtained. The method for the screening is illustrated below.
(1) Isolation of the Gene Encoding the Protein of the Present Invention mRNA was isolated from roots (10 g) of 6-week-old cucumber, and a cDNA library was then synthesized using the mRNA as a template, oligo dT primers and a cDNA preparation kit (Pharmacia). The synthesized cDNAs were individually inserted into λgt11 (Promega) at the EcoRI restriction site to construct the cDNA library.

On the other hand, xylem sap collected from cucumber stem was lyophilized, and then used to immunize rats, thereby giving an anti-serum to the xylem sap. The anti-xylem sap polyclonal antibody was used to screen the cucumber root cDNA expression library. A plasmid containing the positive clone was designated "λXSP4". The λXSP4 DNA was digested with EcoRI to yield a DNA fragment of about 600 bp in length. This DNA fragment was inserted into pUC19, which was designated "pXSP4". The selected clones were determined for their entire nucleotide sequence on a fluorescent sequencer (ABI) using Taq Dye Deoxy Terminator Cycle Sequencing Kit (ABI) (see SEQ ID NO:19). The amino acid sequence of XSP4 was deduced from the determined nucleotide sequence, (see SEQ ID NO:20). As a result, it was assumed that XSP4 had a length of approximately 15 kDa.

Based on the assumption that, among the proteins contained in xylem sap, a protein showing a band corresponding to 15 kDa would be XSP4 protein, xylem sap was concentrated with acetone, and an aliquot (about 300 µl) of the resultant solution was analyzed by SDS-PAGE. Since a protein band corresponding to about 15 kDa was observed on the acrylamide gel, this region was excised from the gel, and then eluted with an elution buffer (0.1M sodium acetate, 0.1% SDS, pH 8.5). The protein (i.e., XSP4) contained in the elution buffer was determined for its N-terminal amino acid sequence on a protein sequencer 377 A (ABI). As a result, it was found that the protein had the amino acid sequence depicted in SEQ ID NO:21. Based on this N-terminal amino acid sequence, a signal sequence of XSP4 could be deduced (see SEQ ID NO:22).

To clone the upstream promoter region of XSP4, TAIL-PCR was performed according to the method described in "The Plant Journal", vol.8, pp.457–463, 1995. At first, based on the nucleotide sequence of XSP4 cDNA determined above, primer 13 (SEQ ID NO:23), primer 14 (SEQ ID NO:24) and primer 15 (SEQ ID NO:25) shown below were synthesized. Using the combination of primer 12 (SEQ ID NO:18) and primer 13 (SEQ ID NO:23) and cucumber genomic DNA as a template, PCR was performed at a program: 93° C. for 1 min.; and 95° C. for 1 min., for 1 cycle; at a program: 94° C. for 1 min.; 60° C. for 1 min.; and 72° C. for 2.5 min., for 5 cycles; at a program: 94° C. for 1 min.; 25° C. for 3 min.; after gradually heating to 72° C. over 3 min., 72° C. for 2.5 min., for 1 cycle; at a program: 94° C. for 1 min.; 68° C. for 1 min.; 72° C. for 2.5 min.; 94° C. for 30 sec.; 68° C. for 1 min.; 72° C. for 2.5 min.; 94° C. for 30 sec.; 44° C. for 1 min., and 72° C. for 2.5 min., for 15 cycles; and then at a program: 72° C. for 2.5 min. for 1 cycle. Using the PCR product as a template in the form of a diluted solution and the combination of primer 12 (SEQ ID NO:18) and primer 14 (SEQ ID NO:24), PCR was performed at a program: 94° C. for 30 sec.; 64° C. for 1 min.; 72° C. for 2.5 min.; 94° C. for 30 sec.; 64° C. for 1 min.; 72° C. for 2.5 min.; 94° C. for 30 sec.; 44° C. for 1 min.; and 72° C. for 2.5 min. for 12 cycles; and then at a program: 72° C. for 2.5 min. for 1 cycle. Using the PCR product as a template in the form of a diluted solution and the combination of primer 12 (SEQ ID NO:18) and primer 15 (SEQ ID NO:25), PCR was performed at a program: 94° C. for 60 sec.; 44° C. for 1 min.; and 72° C. for 2.5 min. for 20 cycles; and then at a program: 72° C. for 5 min. for 1 cycle, thereby yielding an amplified fragment of about 2,000 bp in length.

The entire nucleotide sequence of the resultant fragment was determined on a fluorescent sequencer (ABI) using Taq Dye Deoxy Terminator Cycle Sequencing Kit (ABI) (see SEQ ID NO:2). The result clearly demonstrated that the clone contained a promoter region of about 2,000 bp in length (i.e., a promoter of the present invention; Promoter II).

| Primer 13: 5'-cctacacctccatatccagagccag-3' | (SEQ ID NO:23) |
| Primer 14: 5'-tagcaccaacaccacaccataagg-3' | (SEQ ID NO:24) |
| Primer 15: 5'-gatgtggtggatcataggtgagaag-3' | (SEQ ID NO:25) |

Example 3

Analysis of Expression Pattern of Coding Region Protein by Northern Hybridization Total RNA (about 400 µg) was isolated from each of the stem, leaf, root, seed, fruit and pericarp (20 g, each) of a 5-week-old cucumber using ISOGEN (Nippon Gene). An aliquot (20 µg) of the total RNA was fractionated by electrophoresis on a 1.2% denaturing agarose gel, and then blotted on a Nylon filter (Hybond-N; Amercham) in 20×SSC by the capillary blotting method. After blotting, the filter was dried with air and baked at 80° C. for 2 hours to fix the RNA thereon. The filter was immersed in a pre-hybridization solution (10% dextran sulfate, 2×SSC, 1% SDS) and incubated at 60° C. for 2 hours.

A plasmid DNA was labeled by incorporating therein [$\alpha$-$^{32}$P]dCTP using Random Primer DNA Labeling kit Ver.2 (Takara Shuzo Co., Ltd.), which was used as a probe to perform Northern hybridization on the filter. The resultant filter was analyzed using an image analyzer. As a result, it was confirmed that the protein coding region gene was highly transcribed only in the root, demonstrating that the gene was highly transcribed in the root and secreted into xylem sap.

Example 4

Construction of Expression Vector (1) The 1.9 kb upstream region of XSP30 was amplified from pXSP30 by PCR using primer 16 (SEQ ID NO:26) and primer 17 (SEQ ID NO:27) shown below. The product was cloned into pT7Blue. During the PCR amplification, HindIII- and BamHI-restriction sites were introduced into the amplified fragment. The PCR-amplified fragment was digested with HindIII and BamHI. After the agarose gel electrophoresis, a gel region containing a about 2 kb DNA fragment was excised from the gel, and the DNA fragment was purified therefrom. The fragment was ligated to a binary vector pBI101 (CLONTECH) that had been digested with HindIII and BamHI to give a recombinant vector. *E. coli* JM109 competent cells were transformed with the recombinant vector. The transformants were selected on LB plate containing kanamycin (50 µg/mL). The plasmid DNA was prepared from the grown clones on the plate, and the coding region therein was sequenced in the same manner as described above to determine its structure. The plasmid was designated "pXSP30UP".

On the other hand, a fluorescent protein (GFP) gene derived from a jellyfish (*Aequorea victoria*) was amplified from pEGFP-N1 (CLONTECH) into which the GFP gene had been introduced, by PCR using primer 18 (SEQ ID NO:28) and primer 19 (SEQ ID NO:29). During the PCR amplification, BamHI- and SacI-restriction sites were introduced into the amplified fragment. The PCR-amplification product was cloned into pT7Blue vector, which was designated "pXSP3030".

pXSP3030 was digested with BamHI and SacI. After the agarose gel electrophoresis, a gel region containing an about 0.7 kb DNA fragment was excised from the gel, and the DNA fragment was purified therefrom. The fragment was ligated to pXSP30UP that had been digested with BamHI and SacI to give a recombinant plasmid. *E. coli* JM109 competent cells were transformed with the recombinant plasmid. Positive clones were selected on LB plate containing kanamycin (50 µg/mL). The plasmid DNA was prepared from the grown clones on the plate, and the coding region on the plasmid DNA was then sequenced in the same manner as described above to determine its structure. As a result, it was confirmed that, no nucleotide substitution occurred in the coding region and no change in structure was found in the ligating portions and their surroundings. The plasmid thus prepared was designated "pXSP3038" (see FIG. 1). *E. coli* XL1 Blue containing the plasmid has been deposited under the name "*E. coli* XL1-Blue (pXSP3038)" on Feb. 18, 1999 at the National Institute of Bioscience and Human-technology, Agency of Industrial Science and Technology, Japan (1-3, Higashi 1-chome, Tsukuba-shi, Ibaragi-ken, Japan) under the accession No. FERM BP-6652.

Figure 2:
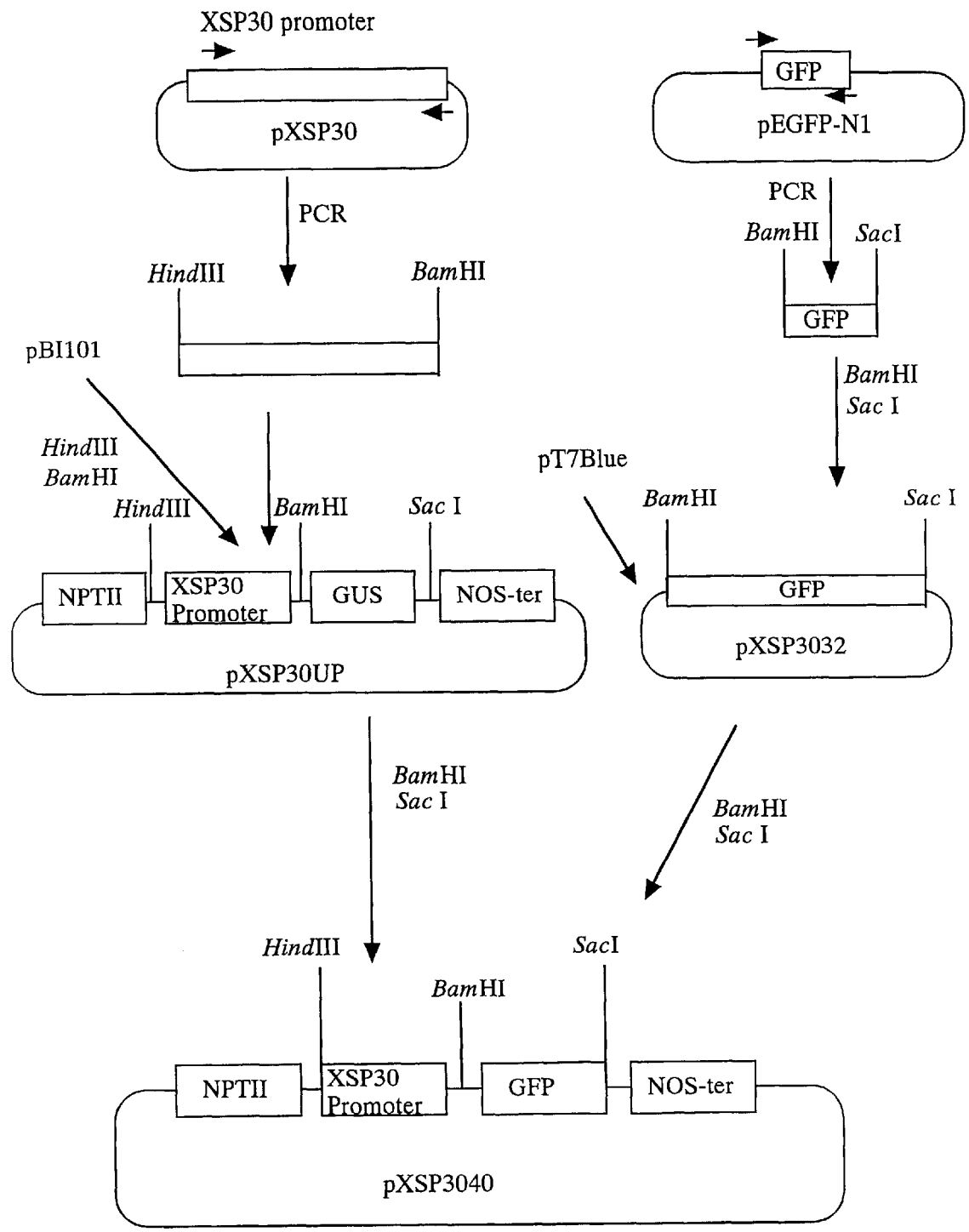
FIG. 2 illustrates the construction of an expression vector pXSP3040.

In the same manner, a GFP gene region without XSP30 signal coding sequence was amplified by PCR using primer 20 (SEQ ID NO:30) and primer 19 (SEQ ID NO:29). The PCR-amplified product was cloned into pT7Blue vector, which was designated "pXSP3032". The plasmid was digested with restriction enzymes and the resultant fragment was ligated to pXSP30UP in the same manner as described above. The resultant plasmid without XSP30 signal coding sequence was designated "pXSP3040" (see FIG. 2).

| | |
|---|---|
| Primer 16: 5'-ccggatcccctttgattactttaattcgac-3' | (SEQ ID NO:26) |
| Primer 17: 5'-ccaagctttggagagtggttatttgggga-3' | (SEQ ID NO:27) |
| Primer 18: 5'-aaggatccatgaaagaaattgtgttgag-catcattgtagccttctcactcaccac-ccaacttgccatcgccatggtgagcaagggcgaggag-3' | (SEQ ID NO:28) |
| Primer 19: 5'-cccgggagctctctagattacttgtacag ctcgtccatgccgag-3' | (SEQ ID NO:29) |
| Primer 20: 5'-aaggatccatggtgagcaagggcgaggag-3' | (SEQ ID NO:30) |

Figure 3:
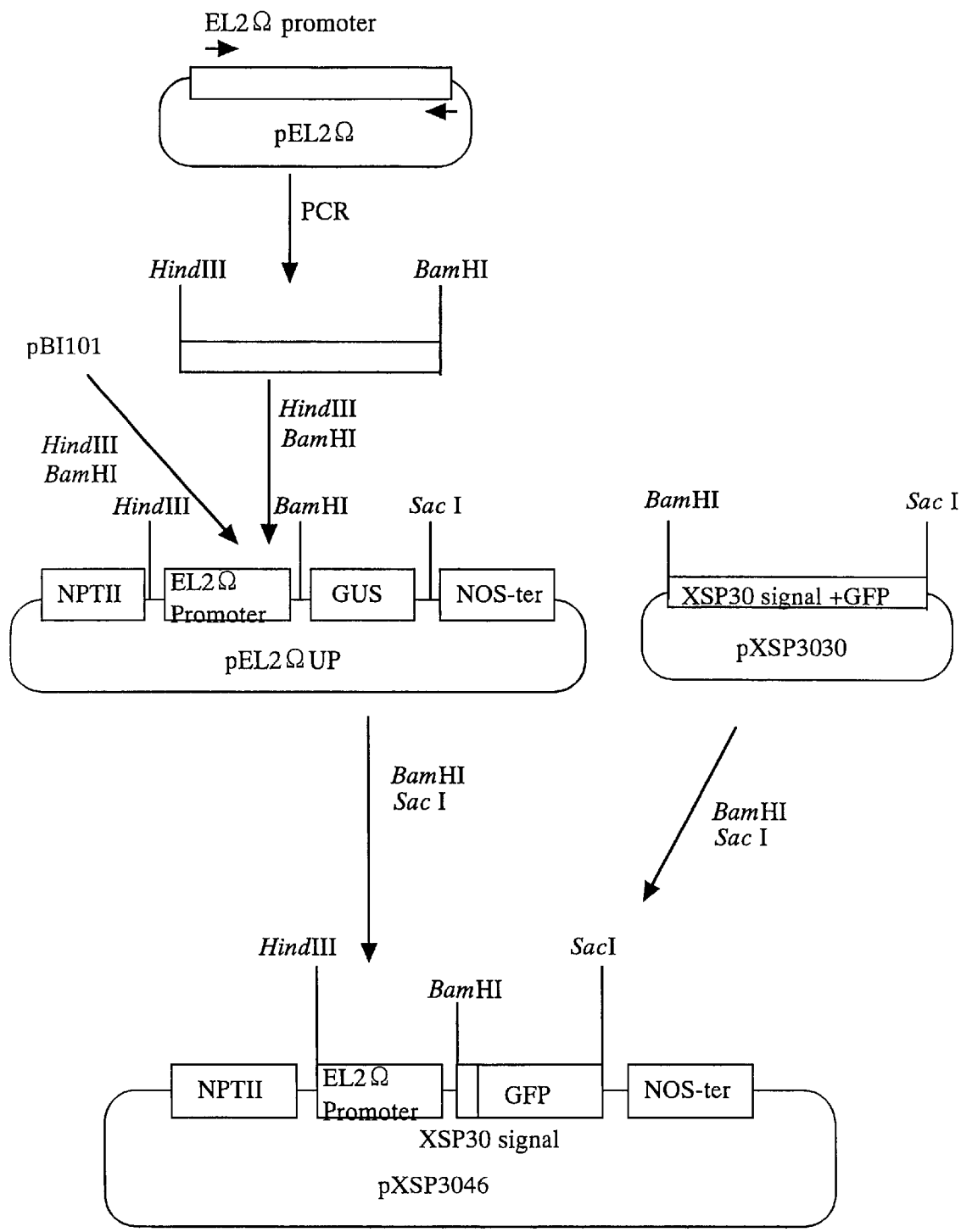
FIG. 3 illustrates the construction of an expression vector pXSP3046.

(2) In the same manner as in (1), a GFP gene was amplified from pEGFP-N1 (CLONTECH) by PCR using primer 18 (SEQ ID NO:28) and primer 19 (SEQ ID NO:29). During the PCR amplification, BamHI- and SacI-restriction sites were introduced into the amplified fragment. The XSP30 signal coding sequence and the GFP gene were inserted into a DNA fragment (El2Ω) (Plant Cell Physiol., 37, 49–59, 1996) having cauliflower mosaic virus 35S promoter and its enhancer at the BamHI- and SacI-restriction sites which were located downstream of El2Ω, thereby ligating the El2Ω romoter, the XSP30 signal peptide coding sequence and the GFP gene. The resultant plasmid was designated "pXSP3046" (see FIG. 3).

Figure 4:
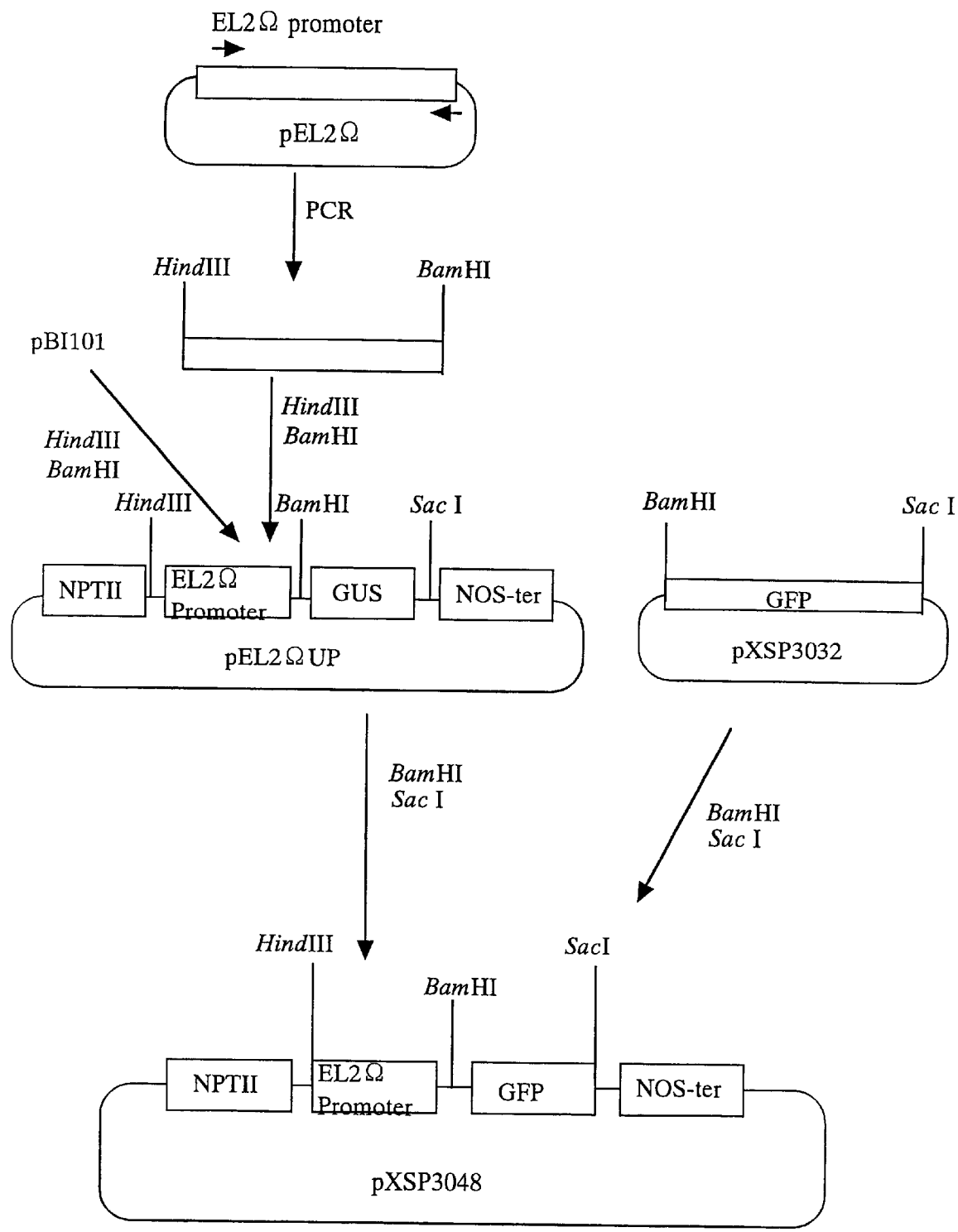
FIG. 4 illustrates the construction of an expression vector pXSP3048.

In the same manner as in (1), a GFP gene without XSP30 signal coding sequence was amplified by PCR using primer 20 (SEQ ID NO:30) and primer 19 (SEQ ID NO:29), inserted into El2Ω at its downstream region. The plasmid without XSP30 signal coding sequence thus prepared was designated "pXSP3048" (see FIG. 4).

*E. coli* JM109 competent cells were transformed with the plasmid. Positive clones were selected on LB plate containing kanamycin (50 µg /mL), and the plasmid DNA was prepared from the grown clones on the plate. The coding region on the plasmid DNA was sequenced to determine its structure. As a result, it was confirmed that no nucleotide substitution occurred in the coding region and the boundary regions and their surroundings had no change in structure.

(3) The 1.9 kb upstream region of XSP4 was amplified from pXSP4 by PCR using primer 21 (SEQ ID NO:31) and primer 22 (SEQ ID NO:32) shown below. The product was cloned into pT7Blue. During the PCR amplification, HindIII- and BamHI-restriction sites were introduced into the amplified fragment. The PCR-amplified product was digested with HindIII and BamHI. After subjecting to agarose gel electrophoresis, a band containing the fragment was excised from the gel, and then purified. The fragment was ligated to a binary vector pBI101 (CLONTECH) that had been digested with HindIII and BamHI, and E. coli JM109 competent cells were transformed with the resultant recombinant vector. The plasmid thus prepared was designated "pXSP4UP".

Figure 5:
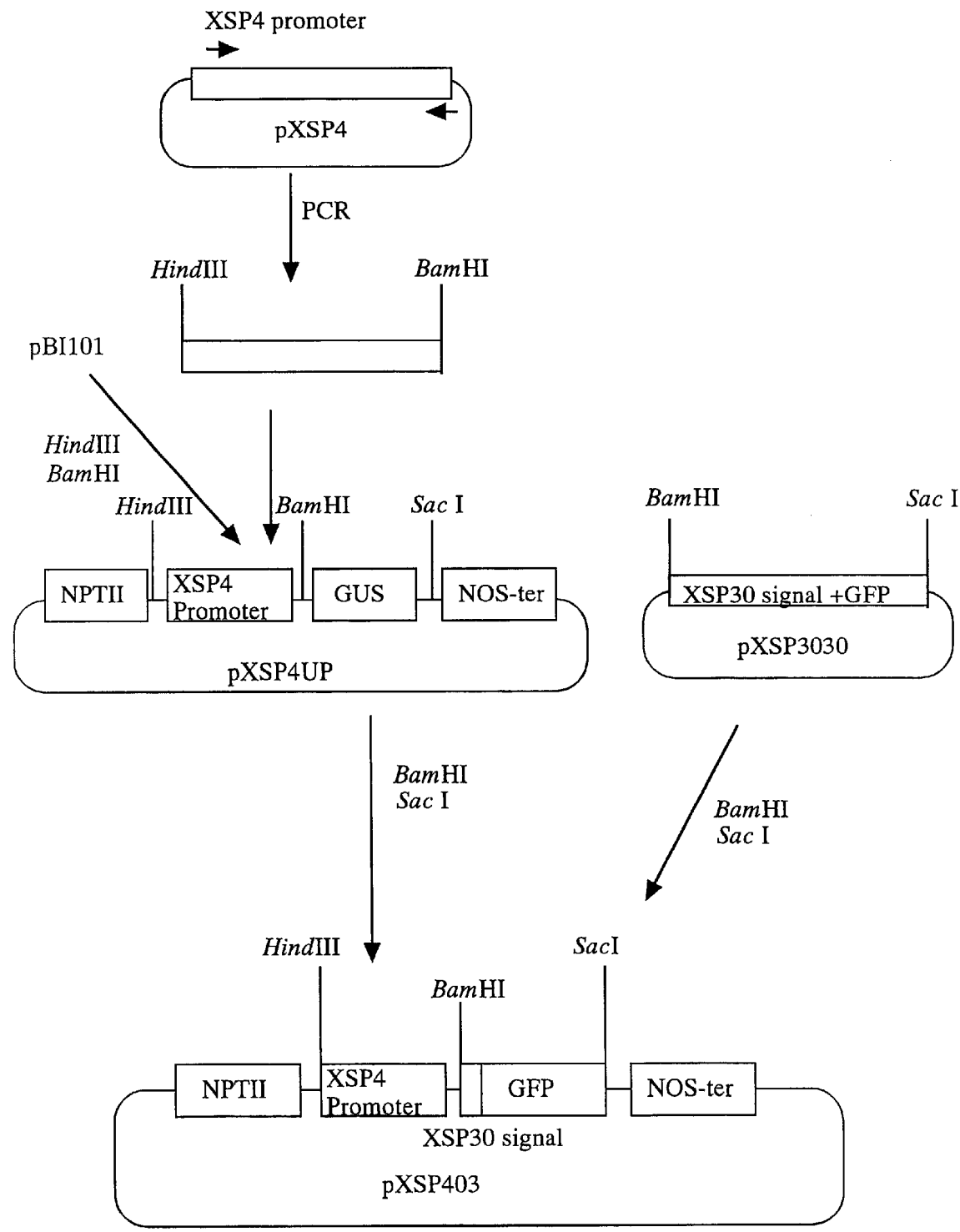
FIG. 5 illustrates the construction of an expression vector pXSP403.

In the same manner as in (1), the amplified GFP gene was ligated to pXSP4UP at the BamHI/SacI restriction sites. E. coli JM109 competent cells were transformed with the resultant plasmid, and the target transformants were selected on LB plate containing kanamycin (50 µg/mL). The plasmid DNA was prepared from the grown clones on the plate. The coding region on the plasmid DNA was sequenced to determine its structure. As a result, it was confirmed that no nucleotide substitution occurred in the coding region and the ligation portions and their surroundings had no change in structure. The plasmid thus prepared was designated "pXSP403" (see FIG. 5).

Primer 21: 5'-ccggatccatttggagaagggatgcctt-3' (SEQ ID NO:31)
Primer 22: 5'-ccaagcttgatgatggtggtgcagaggtga-3' (SEQ ID NO:32)

Figure 6:
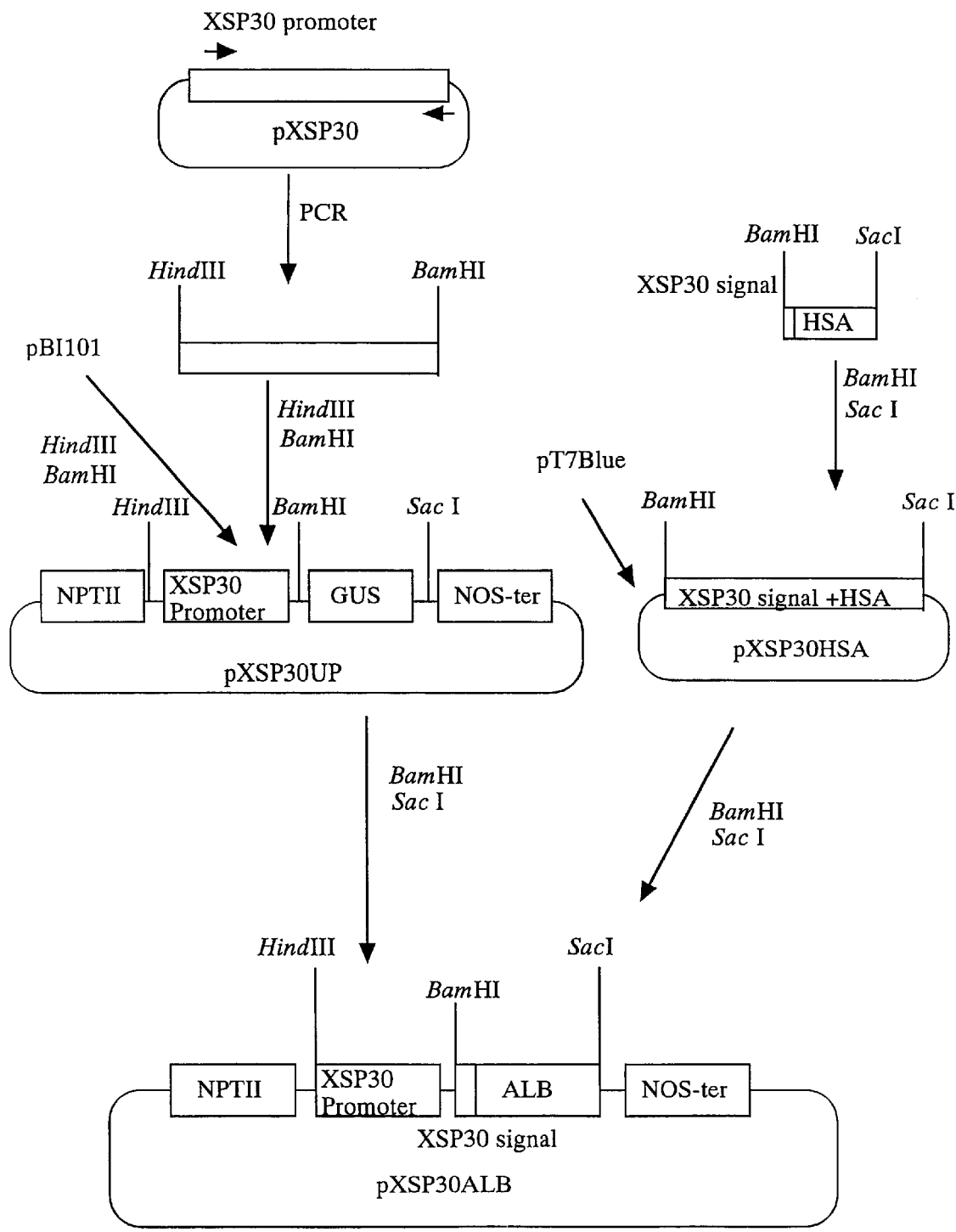
FIG. 6 illustrates the construction of an expression vector pXSP30ALB.

(4) A gene encoding mature human serum albumin protein with the XSP30 signal coding sequence was amplified from a human liver cDNA library (Toyobo Co., Ltd.) by PCR using primer 23 (SEQ ID NO:33) and primer 24 (SEQ ID NO:34) shown below. The PCR-amplified product was inserted into pXSP30UP prepared in (1) at the BamHI/SacI restriction sites. The resultant plasmid was designated "pXSP30ALB" (see FIG. 6).

In the same manner as described above, the coding region on the plasmid was sequenced to determine its structure. As a result, it was confirmed that no nucleotide substitution occurred in the coding region and the ligating portions and their surroundings had no change in structure.

Primer 23: 5'-aaggatccat gaaagaaatt gtgttgagca tcattgtagc cttctcactc
accacccaac ttgccatcgc cgatgcacac
aagagtgagg ttgct-3' (SEQ ID NO:33)
Primer 24: 5'-cccgggagctctctagattataagcctaag
gcagcttgacttgc-3' (SEQ ID NO:34)

Figure 7:
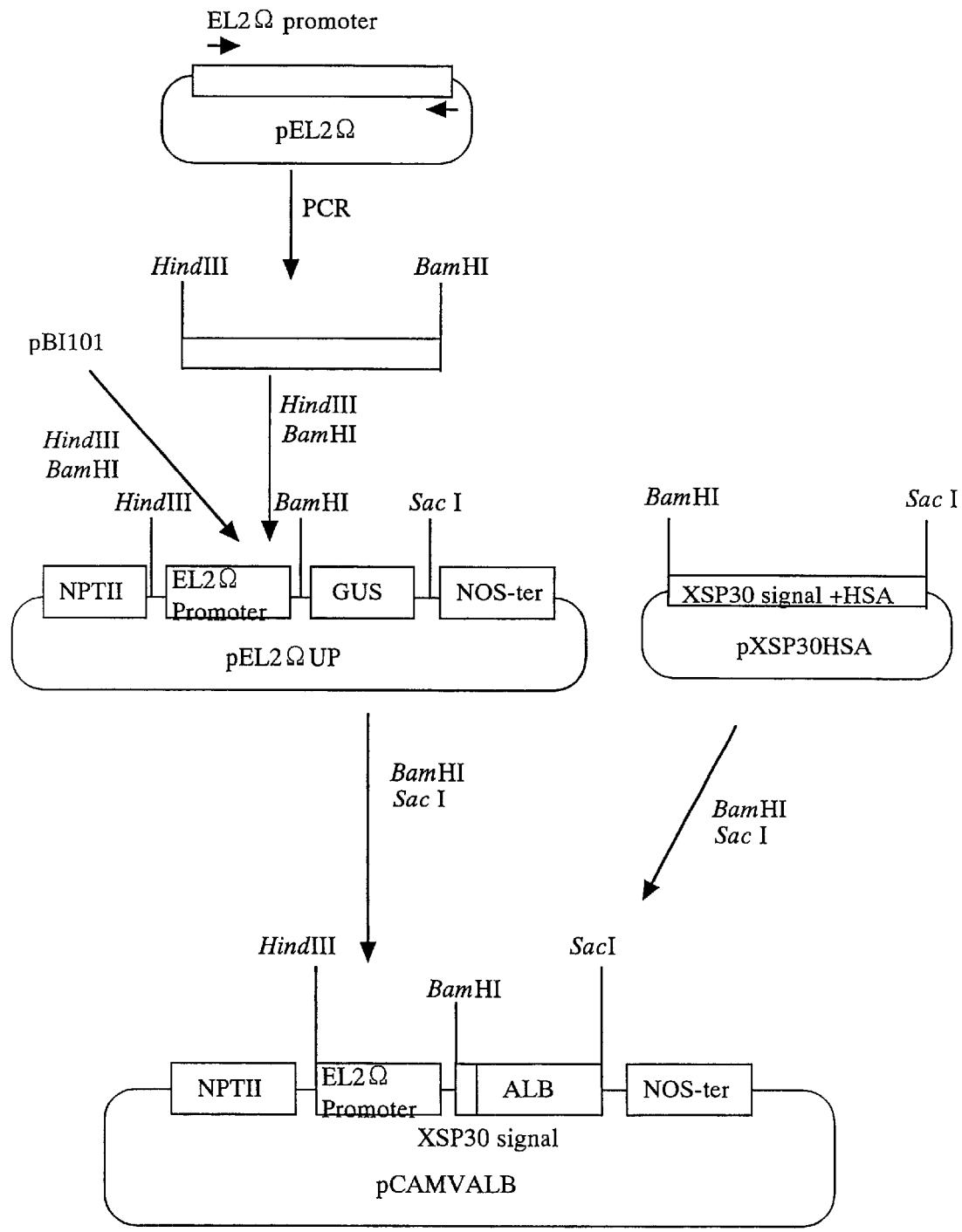
FIG. 7 illustrates the construction of an expression vector PCAMVALB.

(5) In the same manner as described in (4), a gene encoding mature human serum albumin protein with the XSP30 signal coding sequence was amplified from a human liver cDNA library (Toyobo Co., Ltd.) by PCR using primer 23 (SEQ ID NO:33) and primer 24 (SEQ ID NO:34). The PCR-amplified product was inserted into pBI101 at the BamHI/SacI restriction sites. El2Ω was inserted into the plasmid at the upstream HindIII/BamHI restriction sites. The plasmid thus prepared was designated "pCAM-VALB" (see FIG. 7).

E. coli JM109 competent cells were transformed with the plasmid. Transformants were selected on LB plate containing kanamycin (50 µg/mL), and plasmid DNA was prepared from the grown clones on the plate. In the same manner as described above, the coding region in the plasmid was sequenced to determine its structure. As a result, it was confirmed that no nucleotide substitution occurred in the coding region and the ligating portions and their surroundings had no change in structure.

Example 5

Generation of GFP Gene-inserted Plant Body (1) Sterile Sowing

Hulls was removed from mature seeds of Cucumber (*Cucumis sativus* L.) (about 30 seeds) with a knife, and the seeds were then immersed in an antiformin disinfectant solution (diluted to 1% of the available chlorine concentration) for 15 min, thereby to sterilize the surfaces of the seeds. The seeds were washed with sterile distilled water three times and then sown on a solid medium in a Petri dish. The medium was prepared based on MS medium (T. Murashige and F. Skoog, Physiol. Plant, 15, 473, 1962). After the seeds were sown, the plate was shaded and incubated at 28° C. for 24 hours.

(2) Inoculation of a Solution Containing Agrobacterium Cells

Agrobacterium cells that had been cultured with shaking in L medium at 28° C. overnight, were subcultured in a newly prepared L medium successively until the absorption ($OD_{600}$) of the culture medium reached 0.6. The culture medium was centrifuged to collect the cells as a pellet. The cell pellet was suspended in cold sterile distilled water, and the suspension was centrifuged again to collect the cells. This washing procedure was repeated two times, and further repeated additional two times with a glycerol solution in place of the cooled sterile distilled water. The cells were suspended in a 10% glycerol solution to the final concentration of 400-fold, thereby to make the cells competent. Each of the above constructed Ti plasmid expression vectors (pXSP3038, pXSP3040, pXSP3046, pXSP3048, pXSP403, pXSP30ALB, pCAMVALB) was introduced into the competent cells by electroporation, and transformants were selected on L plate containing kanamycin (50 µg/mL). Plasmid DNA was prepared from the grown kanamycin-resistant clones by the alkaline phosphatase method. The plasmid DNA was confirmed for the success in introduction of the Ti plasmid expression vector by electrophoresis on a 1.0% agarose gel and ethidium bromide staining.

Generation of a transgenic cucumber was performed according to the method described in Tabei, Y. et al., Plant Cell Reports, 17: 159–164, 1998 or Nishibayashi, S. et al., Plant Cell Rep., 15:809–814, 1996. By way of example, the procedure according to the method by Tabei et al. is illustrated briefly in the following.

Explants were immersed for 5 min. in a solution containing the Ti plasmid-introduced Agrobacterium cells that had been cultured with shaking in L liquid medium containing kanamycin (100 µg/mL) at 28° C. overnight. The resultant solution was transferred to MS-BA culture medium (i.e., a re-generation medium) containing no antibiotic, and the cells and the explants were co-cultured at 25° C. for 3 days in darkness. After the bacterial cells were removed from the culture medium, the explants were transferred to MS-BAC medium containing kanamycin, thereby to enhance the growth of adventitious buds and, at the same time, to select the transformants in the medium containing kanamycin.

Scions of well-grown re-generated shoots with green stems and leaves were inserted on MS-CK medium to grow, and then acclimerated in a closed greenhouse. Lines that achieved the desired acclimeration population were confirmed for the formation of transformants, and subcultured on MS-CK medium to root.

(3) Identification of Transformants in the Plant Bodies of the Present Invention About four or five leaves from each of the transgenic cucumbers were used to prepare genomic DNAs by the CTAB method.

For each of the transgenic cucumbers transfected with pXSP3038 and pXSP3040, the DNA (50 ng) was used as a template for PCR. The PCR was performed at a program: 94° C. for 1 min.; 55° C. for 2 min.; and 72° C. for 3 min. for 40 cycles using, as primers, the combination of an internal region of GFP gene (i.e., a reporter gene) [primer 17: 5'-ccaagctttggagtggttatttgggga-3' (SEQ ID NO:27)] and a region upstream of codon ATG by 20,000 bp on GFP gene [primer 25: 5'-ttacttgtacagctcgtccat-3' (SEQ ID NO:35)] and the combination of an internal region of GFP gene [primer 20: 5'-aaggatccatggtgagcaagggcgaggag-3' (SEQ ID NO:30)] and an internal region of NOS terminator [primer 26: 5'-catgcttaacgtaattcaacag-3' (SEQ ID NO:36)]. An aliquot of the PCR product was fractionated by electrophoresis on a 0.8% agarose gel to confirm for the success in amplification of the DNA fragment (i.e., the inserted gene).

For each of the transgenic cucumbers transfected with pXSP3046 and pXSP3048, the DNA (50 ng) was used as a template for PCR. The PCR was performed using, as primers, the combination of an internal region of GFP gene (i.e., a reporter gene) [primer 17: 5'-ccaagctttggagtggttatttgggga-3' (SEQ ID NO:27)] and an internal region of El2Ω [primer 27: 5'-acttcatcaaaaggacagta-3'(SEQ ID NO:37)] and the combination of an internal region of GFP gene [primer 20: 5'-aaggatccatggtgagcaagggcgaggag-3' (SEQ ID NO:30)] and an internal region of NOS terminator [primer 26: 5'-catgcttaacgtaattcaacag-3' (SEQ ID NO:36)]. The success in amplification of the DNA fragment (i.e., the inserted gene) was confirmed in the same manner as described above.

For the transgenic cucumber transfected with pXSP403, the DNA (50 ng) was used as a template for PCR. The PCR was performed using, as primers, the combination of an internal region of GFP gene (i.e., a reporter gene) [primer 22: 5'-ccaagcttgatgatggtggtgcagaggtga-3' (SEQ ID NO:32)] and a region upstream of codon ATG by 20,000 bp on GFP gene (i.e., an internal region of the promoter of the present invention) [primer 25: 5'-ttacttgtacagctcgtccat-3' (SEQ ID NO:35)] and the combination of an internal region of GFP gene [primer 19: 5'-cccgggagctctctagattacttgtacagctcgtccaatgccgag-3' (SEQ ID NO:29)] and an internal region of NOS terminator [primer 26: 5'-catgcttaacgtaattcaacag-3' (SEQ ID NO:36)]. The success in amplification of the DNA fragment (i.e., the inserted gene) of interest was confirmed in the same manner as described above.

For the transgenic cucumber transfected with pXSP30ALB, the DNA (50 ng) was used as a template for PCR. The PCR was performed at a program: 94° C. for 1 min.; 55° C. for 2 min.; and 72° C. for 3 min. for 40 cycles using, as primers, the combination of an internal region of human serum albumin gene [primer 16: 5'-ccggatccctttgattactttaattcgac-3' (SEQ ID NO:26)] and a region upstream of human serum albumin gene (an internal region of the promoter of the present invention) [primer 28: 5'-agcaacctcactcttgtgtgc-3' (SEQ ID NO:38)] and the combination of an internal region of human serum albumin gene [primer 5'-aaggatccat gaaagaaatt gtgttgagca tcattgtagc cttctcactc accacccaac ttgccatcgc cgatgcacac aagagtgagg ttgct-3' (SEQ ID NO:33)] and an internal region of NOS terminator [primer 26: 5'-catgcttaacgtaattcaacag-3' (SEQ ID NO:36)]. An aliquot of the PCR product was fractionated by electrophoresis on a 0.8% agarose gel to confirm for the success in amplification of the DNA fragment (i.e., the inserted gene).

For the transgenic cucumber transfected with pCAMVALB, the DNA (50 ng) was used as a template for PCR. The PCR was performed at a program: 94° C. for 1 min.; 55° C. for 2 min.; and 72° C. for 3 min. for 40 cycles using, as primers, the combination of an internal region of human serum albumin gene [primer 27: 5'-acttcatcaaaaggacagta-3' (SEQ ID NO:37)] and a region upstream of human serum albumin gene (an internal region of El2Ω) [primer 28: 5'-agcaacctcactcttgtgtgc-3' (SEQ ID NO:38)] and the combination of an internal region of human serum albumin gene [primer 23: 5'-aaggatccat gaaagaaatt gtgttgagca tcattgtagc cttctcactc accacccaac ttgccatcgc cgatgcacac aagagtgagg ttgct-3' (SEQ ID NO:33)] and an internal region of NOS terminator [primer 26: 5'-catgcttaacgtaattcaacag-3' (SEQ ID NO:36)]. An aliquot of the PCR product was fractionated by electrophoresis on a 0.8% agarose gel to confirm the success in amplification of the DNA fragment (i.e., the inserted gene).

(4) Confirmation of Foreign Protein Secretion in Plant Bodies

Kanamycin-resistant transgenic cucumbers transformed with pXSP403, pXSP3038 and pXSP3046, respectively, were grown for 1 month. The stem of each of the transgenic cucumbers was cut 10 cm above the soil level so as to contain no leaf. The first several drops of the xylem sap (exudate) from the cut surface of the stem were discarded, and the cut surface was washed with sterile water. A tube was connected to the stem to collect the xylem sap in the tube on ice. The collected xylem sap was concentrated with acetone. An aliquot (300 μL) of the xylem sap was analyzed by the SDS-PAGE method. When Western blotting was performed using an anti-GFP antibody, a band corresponding to GFP protein was observed at the position indicating the size of about 27 kDa on the gel. Thus, the success in secretion of the foreign protein in the plant bodies of the present invention could be confirmed.

On the other hand, as controls, kanamycin-resistant transgenic cucumbers transformed with pXSP3040 and pXSP3048 without the signal coding sequence, respectively were used and analyzed in the same manner as described above. As a result, it was confirmed that no band corresponding to GFP protein was confirmed.

Kanamycin-resistant transgenic cucumbers transformed with Pxsp30ALB and pCAMVALB, respectively, were grown for 1 month. The stem of each of the transgenic cucumbers was cut 10 cm above the soil level so as to contain no leaf. The first several drops of the xylem sap (exudate) from the cut surface of the stem were discarded, and the cut surface was washed with sterile water. A tube was connected to the stem to collect the xylem sap in the tube on ice. The collected xylem sap was concentrated with acetone. An aliquot (300 μg L) of the xylem sap was analyzed by SDS-PAGE. When Western blotting was performed using an anti-human serum albumin antibody, a band corresponding to human serum albumin was observed at the position indicating the size of about 60 kDa on the gel. Thus, the success in secretion of the foreign protein in the plant bodies of the present invention could be confirmed.

As described above, according to the present invention, there are provided a method for producing a foreign polypeptide in a plant xylem sap with high efficiency using a plant genetic recombination technique, and a promoter, a signal peptide coding sequence and the like for use in the method. Since the method of the present invention has such an advantage that a foreign polypeptide can be produced with high efficiency, the present invention is extremely useful industrially.

All publications, patents and patent applications cited herein are incorporated herein by reference in their entirety.

What is claimed is:

1. A promoter comprising SEQ ID NO: 1.
2. A promoter comprising SEQ. ID NO: 2.

\* \* \* \* \*

SEQUENCE LISTING

<160> NUMBER OF SEQ ID NOS: 38

<210> SEQ ID NO 1
<211> LENGTH: 2030
<212> TYPE: DNA
<213> ORGANISM: Cucumis sativus

<400> SEQUENCE: 1

| | | | | | |
|---|---|---|---|---|---|
| agtcgagtga | gatgaaaaag | gaaaccacat | ggagagtggt | tatttgggga | agaacatgaa | 60 |
| aataacacga | agaaaaagga | aatcacgtgg | aaaaatggaa | aaggaaatag | aaaaataatt | 120 |
| gagaaaaaga | gaaatgaaac | aattaaaaat | aattgagaaa | aatgaaaaga | aaatcaataa | 180 |
| aaataattga | gaaaaaggaa | aagaaaactg | ataaaaataa | ttgagaaaaa | ggaaaggaaa | 240 |
| ccgataaaaa | taattgagat | aaaaaacgaa | aaggaaacca | acagaaataa | ttaagaaaaa | 300 |
| ggaagaggaa | aagaaatcca | ataaaaataa | ttgagaaacg | gaataggaga | aactattttt | 360 |
| tttcccaata | attccttata | aaattagaaa | tgtttctact | tttttttagga | cgagaaatag | 420 |
| gaaacgttac | caaagacctc | tattgtttct | tagaaaaatg | aaaacagaaa | cataaaacgg | 480 |
| aaaacgagaa | tgttaccaaa | cgactttata | aatttttcat | ttgtaagttc | gaatccattc | 540 |
| aattatattt | tcactttggg | ttaatatttg | gtgattccaa | aatttaaaaa | tataatataa | 600 |
| ttgagaaaaa | ggaaaagaaa | atcgataaaa | gtaattttttt | aaaaaaaaga | aaagaaaact | 660 |
| gataaaaata | atcgagagaa | tggaaaataa | accgataaaa | ataattgaga | aaaagaaaa | 720 |
| gaaaattgat | aaaaataatt | gagaaatgg | aaaagaaaaa | ggaaaccaat | aaaaataatt | 780 |
| gagaaacaga | actaaagaaa | atatttttttt | ctcccaataa | ccttttttata | aaattccaaa | 840 |
| cgtttctatt | tttaaagaaa | caagaaccag | cacctgtgct | tactagacat | gttctaatgc | 900 |
| ttaagttaga | aaacatacat | gtgcaataag | agctagaaag | gttgagtatt | atcggtgact | 960 |
| tatatttttt | taaataatca | tgatgtattt | atagatataa | ttgacttata | acctttctct | 1020 |
| tagggtatgt | atttgcatta | gacttatcct | ttctagggtt | aaccttttgc | tatattatgg | 1080 |
| gcttaagata | aacccttgga | tgaggcatgt | tctagcagac | attttgtcaa | ttttttctgat | 1140 |
| cggacatgct | agtttaggcc | aagtccgtgc | aaactaatac | ctatcactag | gtccattttg | 1200 |
| atcatatgcc | atgttgccac | ttctgactca | aattatatat | tatcttctta | acttctgtta | 1260 |
| tctcttgtct | ataaatgtca | atattatgtc | tcaccatcgg | ttccttgtaa | caatatttat | 1320 |
| cccaaaattt | atcatcacat | tataccccat | aaatctttcg | taagagatat | tatcctagaa | 1380 |
| aagtatgcct | atagggttgg | aaaatctttc | tattaagtag | gtacaaaagt | agtgaaataa | 1440 |
| aattcaaatt | tatatgttta | cttgcatggc | caatgtaaca | acaaaaaata | ataatgtaga | 1500 |
| aacatggtct | atattaaata | ataaatagag | taagataaat | caaaatatttt | ataaatatag | 1560 |
| caatatttta | cttttttactt | acgatagatc | gtggttgact | aatttctatg | ttttaatggg | 1620 |
| tctatatata | ataatttaaa | gataataaat | tgtgatattt | tgttatattt | ataaatatttt | 1680 |
| ttaatcacat | ttaaaacaaa | tttccattca | ctccactaaa | ctatgaattt | catcctaatt | 1740 |
| accactgcaa | aatgtaacaa | aaagttcaaa | ccaatgggga | gagtttatgt | gtatactcat | 1800 |
| ccccataaac | aaccccatcc | attggaagaa | caattatgga | tttgtgattc | atcattcccc | 1860 |
| actacaataa | ttttttttttgt | gatccttttt | aattagaata | ataatgcttg | ttccattcat | 1920 |
| aattgtccac | tgggctagcc | tttcgttgta | ttttgtgtgt | atatataccc | cttcattcta | 1980 |
| gcccaacttt | gtcaaacaaa | tatatatagt | cgaattaaag | taatcaaagg | | 2030 |

<210> SEQ ID NO 2
<211> LENGTH: 1835
<212> TYPE: DNA
<213> ORGANISM: Cucumis sativus

<400> SEQUENCE: 2

| | | | | | |
|---|---|---|---|---|---|
| gttcgagtca | gatgttggat | gaattttgtt | cgaataaaaa | ttaaaacaac | ttattgttat | 60 |
| caacttataa | gttatatata | tgatgatggt | ggtgcagagg | tgaaaactta | gtttgagatc | 120 |
| tctccctaca | tctactatgc | ttttacgttc | taatgtattt | tgtggtaaaa | aaatcaatta | 180 |
| taaactttta | agaaaaattt | tcatatgtta | ttatttttc | tctaaattct | aaactagcca | 240 |
| ggttatcaac | aaaacaaata | ccactagagt | ttaagggatt | aggaagcata | tatgaatatc | 300 |
| tcaacttggt | taacacgtcg | tttttaaaca | tttctcatca | ggttgctgtt | tcaaaagtga | 360 |
| tgcactgatg | tgaagaaaca | tataggagaa | aagtgagtgg | aaagttagta | tattggacag | 420 |
| agtacatagt | acatagtagg | tttattatta | atttatccaa | tgataatctc | cttaccagca | 480 |
| ctatgtgatt | tagatatgga | taaaatgtga | tcatttttcc | accactatta | catagcaaat | 540 |
| gggaaaacat | ctcattgtgg | tttgatattt | taaaaaacaa | ttatggtaat | gccagtcgtc | 600 |
| tcatatccca | taatattatc | tcagtctcat | ggcgactgat | acaaaaggac | aaaactaact | 660 |
| tcattaaaat | atgttctctc | cttcctacac | tttttaggta | tatatcattc | atatattaat | 720 |
| cactgcaatt | ggttaggtgg | actacaaaaa | catagatata | gtccgagata | aaattaagta | 780 |
| cggttatatt | ttacgagact | tttgatgtgt | ttgattacat | tttcatgtgt | ttctttttaga | 840 |
| aaataagtta | ttttgaaaaa | actaaagtat | tttaaacaat | ttttagaaca | atcaatttct | 900 |
| tgaaaaatat | tttttcttta | attcaatcta | agatggatcc | tcaaaatatt | tgagggtagt | 960 |
| tcttttataa | aagtatttac | actaggttgg | tttatgaagt | aaaatattga | tcggtaaatt | 1020 |
| caagttttaa | attagaaaaa | ttgaatattt | ctaaaaatag | aagaattggc | taactattta | 1080 |
| caactcatac | caaaatttta | atacaaatcc | aaagtatcta | ttttttattt | tattattatt | 1140 |
| attattttt | gctataggat | gtaaatacta | cctgttttct | tgtaaatttc | tcttacaatc | 1200 |
| ctctacgaga | aagtcttaat | ttttatattt | atgatttata | ttataatata | attatttgga | 1260 |
| accatataat | aaataaaagg | aaaattgtaa | aacataacat | ttgacaaaat | atcttcgtag | 1320 |
| aaaaatttgt | tgtgtaatca | attttgaggt | tttgttatat | ggagcgtaaa | tattttgtca | 1380 |
| aattttctat | ttgtgaaaaa | aaaacttata | ggtaatttga | aagtaagtg | atcttgttta | 1440 |
| agatccaaat | ttcttttatg | aaagtttaat | ttagaataca | tacgagaaaa | atagattaat | 1500 |
| ctagaatgat | aaatgtaaga | taggtttggg | aagtaccaat | aattttaggc | atgtgataga | 1560 |
| ctataactgt | gaagatatat | agtctattgc | tatcttgatg | gctcattctt | gtttgaaaat | 1620 |
| gaccttattt | aaaacacaac | ttttttataa | agaaatccct | tgcatcattc | aaacaatctt | 1680 |
| acagatcgta | ttagtggaag | atgagataga | attctgacat | gtgtattatt | agtatacttg | 1740 |
| aatagtttct | tatctcaactt | ttgagcaagt | agtggagaag | ctgatcatga | accctaaacc | 1800 |
| caccgtatca | ttcactatat | aaaggagatc | actac | | | 1835 |

<210> SEQ ID NO 3
<211> LENGTH: 21
<212> TYPE: PRT
<213> ORGANISM: Cucumis sativus

<400> SEQUENCE: 3

```
Met Lys Glu Ile Val Leu Ser Ile Ile Val Ala Phe Ser Leu Thr Thr
 1               5                  10                  15

Gln Leu Ala Ile Ala
            20
```

<210> SEQ ID NO 4
<211> LENGTH: 25
<212> TYPE: PRT
<213> ORGANISM: Cucumis sativus

<400> SEQUENCE: 4

```
Val Pro Pro Asn Tyr Gly Tyr Gly Val Gly Tyr Gly Gly Val Pro Gly
 1               5                  10                  15

Ala Thr His Leu Val Gly Arg Asp Gly
            20                  25
```

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Designed
      DNA(sense) degenerated from the N-terminal amino acid sequence
      for amplification of a part of cDNA
<221> NAME/KEY: modified_base
<222> LOCATION: (3)
<223> OTHER INFORMATION: a, g, c or t
<221> NAME/KEY: modified_base
<222> LOCATION: (6)
<223> OTHER INFORMATION: a, g, c or t
<221> NAME/KEY: modified_base
<222> LOCATION: (9)
<223> OTHER INFORMATION: a, g, c or t
<221> NAME/KEY: modified_base
<222> LOCATION: (18)
<223> OTHER INFORMATION: a, g, c or t

<400> SEQUENCE: 5
gtnccnggna aytayggnta ygg                                       23

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Designed
      DNA(sense) degenerated from the N-terminal amino acid sequence
      for amplification of a part of cDNA
<221> NAME/KEY: modified_base
<222> LOCATION: (6)
<223> OTHER INFORMATION: a, g, c or t
<221> NAME/KEY: modified_base
<222> LOCATION: (9)
<223> OTHER INFORMATION: a, g, c or t
<221> NAME/KEY: modified_base
<222> LOCATION: (12)
<223> OTHER INFORMATION: a, g, c or t
<221> NAME/KEY: modified_base
<222> LOCATION: (18)
<223> OTHER INFORMATION: a, g, c or t
<221> NAME/KEY: modified_base
<222> LOCATION: (21)
<223> OTHER INFORMATION: a, g, c or t
<221> NAME/KEY: modified_base
<222> LOCATION: (24)
<223> OTHER INFORMATION: a, g, c or t

<400> SEQUENCE: 6
tayggngtng gntayggngg ngtncc                                    26

```
<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Designed
      DNA for amplification of a part of XSP30 cDNA in the 3' RACE

<400> SEQUENCE: 7
cagaagaatg acggaaccat a                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Designed
      DNA for a reverse transcription of a part of XSP30 cDNA

<400> SEQUENCE: 8
agaagtcaag caatagtttt t                                              21

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Designed
      DNA for amplification of a part of XSP30 cDNA in the 1st step
      of 5' RACE

<400> SEQUENCE: 9
aaaaacttca gcagccaa                                                  18

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Designed
      DNA for amplification of a part of XSP30 cDNA in the 1st step
      of 5' RACE

<400> SEQUENCE: 10 gggtcataa ataaagca                                                   18

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Designed
      DNA for amplification of a part of XSP30 cDNA in the 1st step
      of 5' RACE

<400> SEQUENCE: 11
agcaaaattt atcattca                                                  18

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Designed
      DNA for amplification of a part of XSP30 cDNA in the 2nd step
      of 5' RACE

<400> SEQUENCE: 12
```

-continued

```
gtagtaagtg agtgtggt                                                   18

<210> SEQ ID NO 13
<211> LENGTH: 1065
<212> TYPE: DNA
<213> ORGANISM: Cucumis sativus

<400> SEQUENCE: 13
atagtcgaat taaagtaatc aaaggatgaa agaaattgtg ttgagcatca ttgtagcctt      60
ctcactcacc acccaacttg ccatcgcagt gccccccaac tatggatatg agttggata     120 tggaggcgtc cctggagcca cacatcttgt gggtcgagat ggattgtgtt tagagatgtc     180
tccatggtac aaacctgcag gtattaattt tccaactcga ttatcaccat gtgacgagaa     240
gaaacaaact caattatgga cgattgtcgg agatggcaca attcgaccca tgaatgataa     300
attttgcttg gctgctgaag ttttttatgg ggtcataaat aaagcagtag taagtgagtg     360
tggtaaagta tcagatccta caagaaatg gacccagaag aatgacggaa ccatagccct     420
cgtcgattca agaatggttc taacaggaga tttagactat gtgacattgc aaagtaacaa     480
atatacacca tcacaaagtt gggaagtcac ggaaagttta aactcaatgg ttgcaaacat     540
cgaatggctt aacaacttgt gtttgcaatc cacagacgat tcaagtcatg tgggattgaa     600
tggatgtaat acagacaata agtaccaaag atgggcattg tatgcagatg gaaccattcg     660
acaacatgtg aacaaaaact attgcttgac ttctgaccaa gattttggtc gctttgtagt     720
tgtgtctaaa tgtgaagaca aaccgcaaca acgttggagt cttgatgcta agactatac     780 tattgaccat cccaacactg acatggtcct agatgtgttt agtgtgcctg attctacttt     840
tccgtcagta ctcgttacga accgtcgtga tggaagtgct agccaaagat ggactattat     900
taactaatga atcagataaa taagataggg gagatgtgaa tccacacgaa ctcatgcatg     960
caaatgcctt tctacttctt taactctctt tctaatgctt aatgtatgaa catcaataaa    1020
ttaataagat aagtgtggat ttatgtgttt aaaaaaaaaa aaaaa                    1065

<210> SEQ ID NO 14
<211> LENGTH: 293
<212> TYPE: PRT
<213> ORGANISM: Cucumis sativus

<400> SEQUENCE: 14

Met Lys Glu Ile Val Leu Ser Ile Ile Val Ala Phe Ser Leu Thr Thr
  1               5                  10                  15

Gln Leu Ala Ile Ala Val Pro Pro Asn Tyr Gly Tyr Gly Val Gly Tyr
             20                  25                  30

Gly Gly Val Pro Gly Ala Thr His Leu Val Gly Arg Asp Gly Leu Cys
         35                  40                  45

Leu Glu Met Ser Pro Trp Tyr Lys Pro Ala Gly Ile Asn Phe Pro Thr
     50                  55                  60

Arg Leu Ser Pro Cys Asp Glu Lys Lys Gln Thr Gln Leu Trp Thr Ile
 65                  70                  75                  80

Val Gly Asp Gly Thr Ile Arg Pro Met Asn Asp Lys Phe Cys Leu Ala
                 85                  90                  95

Ala Glu Val Phe Tyr Gly Val Ile Asn Lys Ala Val Val Ser Glu Cys
            100                 105                 110

Gly Lys Val Ser Asp Pro Asn Lys Lys Trp Thr Gln Lys Asn Asp Gly
        115                 120                 125

Thr Ile Ala Leu Val Asp Ser Arg Met Val Leu Thr Gly Asp Leu Asp
```

```
            130                 135                 140
Tyr Val Thr Leu Gln Ser Asn Lys Tyr Thr Pro Ser Gln Ser Trp Glu
145                 150                 155                 160

Val Thr Glu Ser Leu Asn Ser Met Val Ala Asn Ile Glu Trp Leu Asn
                165                 170                 175

Asn Leu Cys Leu Gln Ser Thr Asp Asp Ser Ser His Val Gly Leu Asn
                180                 185                 190

Gly Cys Asn Thr Asp Asn Lys Tyr Gln Arg Trp Ala Leu Tyr Ala Asp
                195                 200                 205

Gly Thr Ile Arg Gln His Val Asn Lys Asn Tyr Cys Leu Thr Ser Asp
            210                 215                 220

Gln Asp Phe Gly Arg Phe Val Val Ser Lys Cys Glu Asp Lys Pro
225                 230                 235                 240

Gln Gln Arg Trp Ser Leu Asp Ala Lys Asp Tyr Thr Ile Asp His Pro
                245                 250                 255

Asn Thr Asp Met Val Leu Asp Val Phe Ser Val Pro Asp Ser Thr Phe
                260                 265                 270

Pro Ser Val Leu Val Thr Asn Arg Arg Asp Gly Ser Ala Ser Gln Arg
                275                 280                 285

Trp Thr Ile Ile Asn
        290

<210> SEQ ID NO 15
<211> LENGTH: 25
<212> TYPE: DNA
<213> ORGANISM: Artificial Sequence
<220> FEATURE:
<223> OTHER INFORMATION: Designed DNA for amplification of an
      upstream promoter region of XSP30 in the TAIL-PCR

<400> SEQUENCE: 15
tcttctgggt ccatttcttg ttagg                                          25

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Designed
      DNA for amplification of an upstream promoter region of XSP30
      in the TAIL-PCR

<400> SEQUENCE: 16
ctttccgtga cttcccaact ttgtg                                          25

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Designed
      DNA for amplification of an upstream promoter region of XSP30
      in the TAIL-PCR

<400> SEQUENCE: 17
cgtcacatgg tgataatcga gttgg                                          25

<210> SEQ ID NO 18
<211> LENGTH: 16
<212> TYPE: DNA
<213> ORGANISM: Artificial Sequence
<220> FEATURE:
```

<223> OTHER INFORMATION: Description of Artificial Sequence: Designed
      DNA for amplification of an upstream promoter region of XSP30
      in the TAIL-PCR
<221> NAME/KEY: modified_base
<222> LOCATION: (1)
<223> OTHER INFORMATION: a, g, c or t
<221> NAME/KEY: modified_base
<222> LOCATION: (11)
<223> OTHER INFORMATION: a, g, c or t

<400> SEQUENCE: 18
ngtcgaswga nawgaa                                                        16

<210> SEQ ID NO 19
<211> LENGTH: 504
<212> TYPE: DNA
<213> ORGANISM: Cucumis sativus

<400> SEQUENCE: 19
atgcattcta aggcatccct tctccaaatg gctatcttta gaactttctc tttcggtttt        60
cttttgttgg tgagtttagg cttagcttct gcgaccagaa gtcttctcac ctatgatcca       120
ccacatcact ctgtatatga tgatcataac actaaagtag gttacggacg tgaccatcat       180
gatcaacctt atggtggtgg tgttggtgct agtggaggat atggagccgg agctggctct       240
ggatatggag gtgtaggata cgaacatgac catcatgatg gatacgaacg tgatcatgat       300
cgatcttatg gtggtagtgc tggtggagga tatggagttg gagctggctc ctctcttgga       360
ggctctggat atgaaacgt agatcatggg gttggttata gcaatggtgg aagtggtgga       420
tatggagctg gtgttggctc tgaccttggt ggtagcggat atggaagcgg taatggcgga       480
caagtggaag tggaaatggt gatt                                              504

<210> SEQ ID NO 20
<211> LENGTH: 168
<212> TYPE: PRT
<213> ORGANISM: Cucumis sativus

<400> SEQUENCE: 20

Met His Ser Lys Ala Ser Leu Leu Gln Met Ala Ile Phe Arg Thr Phe
  1               5                  10                  15

Ser Phe Gly Phe Leu Leu Leu Val Ser Leu Gly Leu Ala Ser Ala Thr
                 20                  25                  30

Arg Ser Leu Leu Thr Tyr Asp Pro Pro His His Ser Val Tyr Asp Asp
             35                  40                  45

His Asn Thr Lys Val Gly Tyr Gly Arg Asp His His Asp Gln Pro Tyr
         50                  55                  60

Gly Gly Gly Val Gly Ala Ser Gly Gly Tyr Gly Ala Gly Ala Gly Ser
 65                  70                  75                  80

Gly Tyr Gly Gly Val Gly Tyr Glu His Asp His His Asp Gly Tyr Glu
                 85                  90                  95

Arg Asp His Asp Arg Ser Tyr Gly Gly Ser Ala Gly Gly Gly Tyr Gly
            100                 105                 110

Val Gly Ala Gly Ser Ser Leu Gly Gly Ser Gly Tyr Gly Asn Val Asp
            115                 120                 125

His Gly Val Gly Tyr Ser Asn Gly Gly Ser Gly Gly Tyr Gly Ala Gly
        130                 135                 140

Val Gly Ser Asp Leu Gly Gly Ser Gly Tyr Gly Ser Gly Asn Gly Gly
145                 150                 155                 160

Gln Val Glu Val Glu Met Val Ile

-continued

```
                           165

<210> SEQ ID NO 21
<211> LENGTH: 10
<212> TYPE: PRT
<213> ORGANISM: Cucumis sativus

<400> SEQUENCE: 21

Thr Arg Ser Leu Leu Thr Tyr Asp Pro Pro
  1               5                  10

<210> SEQ ID NO 22
<211> LENGTH: 31
<212> TYPE: PRT
<213> ORGANISM: Cucumis sativus

<400> SEQUENCE: 22

Met His Ser Lys Ala Ser Leu Leu Gln Met Ala Ile Phe Arg Thr Phe
  1               5                  10                  15

Ser Phe Gly Phe Leu Leu Leu Val Ser Leu Gly Leu Ala Ser Ala
             20                  25                  30

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Designed
      DNA for amplification of an upstream promoter region of XSP4
      in the TAIL-PCR

<400> SEQUENCE: 23
cctacacctc catatccaga gccag                                          25

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Designed
      DNA for amplification of an upstream promoter region of XSP4
      in the TAIL-PCR

<400> SEQUENCE: 24
tagcaccaac accaccacat aagg                                           24

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence: Designed
      DNA for amplification of an upstream promoter region of XSP4
      in the TAIL-PCR

<400> SEQUENCE: 25
gatgtggtgg atcataggtg agaag                                          25

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Designed
      DNA for amplification of an upstream promoter region of XSP30

<400> SEQUENCE: 26
```

```
ccggatcccc tttgattact ttaattcgac                                    30
```

<210> SEQ ID NO 27
<211> LENGTH: 29
<212> TYPE: DNA
<213> ORGANISM: Artificial Sequence
<220> FEATURE:
<223> OTHER INFORMATION: Description of Artificial Sequence: Designed
      DNA for amplification of an upstream promoter region of XSP30

<400> SEQUENCE: 27

```
ccaagctttg gagagtggtt atttgggga                                     29
```

<210> SEQ ID NO 28
<211> LENGTH: 92
<212> TYPE: DNA
<213> ORGANISM: Artificial Sequence
<220> FEATURE:
<223> OTHER INFORMATION: Description of Artificial Sequence: Designed
      DNA for amplification of GFP gene

<400> SEQUENCE: 28

```
aaggatccat gaaagaaatt gtgttgagca tcattgtagc cttctcactc accacccaac   60
ttgccatcgc catggtgagc aagggcgagg ag                                 92
```

<210> SEQ ID NO 29
<211> LENGTH: 44
<212> TYPE: DNA
<213> ORGANISM: Artificial Sequence
<220> FEATURE:
<223> OTHER INFORMATION: Description of Artificial Sequence: Designed
      DNA for amplification of GFP gene

<400> SEQUENCE: 29

```
cccgggagct ctctagatta cttgtacagc tcgtccatgc cgag                    44
```

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence: Designed
      DNA for amplification of GFP gene

<400> SEQUENCE: 30

```
aaggatccat ggtgagcaag ggcgaggag                                     29
```

<210> SEQ ID NO 31
<211> LENGTH: 28
<212> TYPE: DNA
<213> ORGANISM: Artificial Sequence
<220> FEATURE:
<223> OTHER INFORMATION: Description of Artificial Sequence: Designed
      DNA for amplification of an upstream promoter region of XSP4

<400> SEQUENCE: 31

```
ccggatccat ttggagaagg gatgcctt                                      28
```

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Designed
      DNA for amplification of an upstream promoter region of XSP4

```
<400> SEQUENCE: 32
ccaagcttga tgatggtggt gcagaggtga                                          30

<210> SEQ ID NO 33
<211> LENGTH: 95
<212> TYPE: DNA
<213> ORGANISM: Artificial Sequence
<220> FEATURE:
<223> OTHER INFORMATION: Description of Artificial Sequence: Designed
      DNA for amplification of a human serum albumin gene

<400> SEQUENCE: 33
aaggatccat gaaagaaatt gtgttgagca tcattgtagc cttctcactc accacccaac         60
ttgccatcgc cgatgcacac aagagtgagg ttgct                                    95

<210> SEQ ID NO 34
<211> LENGTH: 44
<212> TYPE: DNA
<213> ORGANISM: Artificial Sequence
<220> FEATURE:
<223> OTHER INFORMATION: Description of Artificial Sequence: Designed
      DNA for amplification of a human serum albumin gene

<400> SEQUENCE: 34
cccgggagct ctctagatta taagcctaag gcagcttgac ttgc                          44

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Designed
      DNA for amplification of an upstream promoter region of XSP30

<400> SEQUENCE: 35
ttacttgtac agctcgtcca t                                                   21

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Designed
      DNA for amplification of GFP gene

<400> SEQUENCE: 36
catgcttaac gtaattcaac ag                                                  22

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Designed
      DNA for amplification of CaMV35S promoter region

<400> SEQUENCE: 37
acttcatcaa aaggacagta                                                     20

<210> SEQ ID NO 38
<211> LENGTH: 21
```

```
<212> TYPE: DNA
<213> ORGANISM: Artificial Sequence
<220> FEATURE:
<223> OTHER INFORMATION: Description of Artificial Sequence: Designed
      DNA for amplification of CaMV35S promoter region

<400> SEQUENCE: 38
agcaacctca ctcttgtgtg c                                          21
```